US006184196B1

(12) United States Patent
Bazin et al.

(10) Patent No.: US 6,184,196 B1
(45) Date of Patent: Feb. 6, 2001

(54) SUCROSE BASED SURFACTANTS AND METHODS THEREOF

(75) Inventors: Helene G. Bazin, Muscatine; Tulay Polat; Robert J. Linhardt, both of Iowa City, all of IA (US)

(73) Assignee: University of Iowa Research Foundation, Iowa City, IA (US)

( * ) Notice: Under 35 U.S.C. 154(b), the term of this patent shall be extended for 0 days.

(21) Appl. No.: 09/321,225

(22) Filed: May 27, 1999

Related U.S. Application Data

(60) Provisional application No. 60/086,756, filed on May 27, 1998.

(51) Int. Cl.[7] .............................. C07H 11/00; C07H 23/00

(52) U.S. Cl. ........................ 510/470; 510/276; 510/290; 510/42; 514/53; 536/4.1; 536/115; 536/122

(58) Field of Search ........................... 536/4.1, 122, 115; 510/472, 276, 290, 470; 514/53

(56) References Cited

U.S. PATENT DOCUMENTS

| 3,808,200 | 4/1974 | Bistline et al. ................... 260/234 R |
| 4,242,364 | 12/1980 | Buddemeyer et al. ................ 426/98 |
| 4,794,015 | 12/1988 | Fujita et al. ........................... 426/589 |
| 5,378,834 | 1/1995 | Koerts et al. ......................... 536/127 |
| 5,447,729 | 9/1995 | Belenduik et al. ................... 424/490 |

FOREIGN PATENT DOCUMENTS

| 230023 | 7/1987 | (EP) .............................. A61K/31/70 |
| WO96/03413 | 2/1996 | (WO) ............................. C07H/15/04 |

OTHER PUBLICATIONS

S. David et al., "The Crystal and Molecular Structure of a Carbohydrate–Derived Stannylene. A Discussion of the Regiospecific Reactions of Dialkyltin Derivatives of Vicinal Diols", Nouveau Journal de Chimie, vol. 3, 1979, pp. 63–68.
T. Bruce Grindley et al., "The structures and reactions of stannylene acetals from carbohydrate–derived trans–diols. Part I. In the absence of added nucleophiles", Can. J. Chem., vol. 68, 1990, pp. 1007–1019.
T. Bruce Grindley et al., "Oligomerization Equilibria and Dynamics of 2,2–Di–n–butyl–1,3,2–dioxastannolanes", J. Am. Chem. Soc., 1990, vol. 112, pp. 1364–1373.
R. M. Munavu et al., "Selective Formation of 2 Esters of Some Methyl α–D–Hexopyranosides via Dibutylstannylene Derivatives", J. Org. Chem., vol. 41, No. 10, 1976, pp. 1832–1836.
M. Berthollet, "Considerations Sur Les Experiences de M. Priestley", Am. Chim. Phys., vol. 3, 1860, pp. 63–114.
F. H. Otey et al., "Preparation of 3–Stearoyl–D–Glucose—A Bread–Softening Agent", J. Am. Oil. Chem. Soc., vol. 35, Sep. 1958, pp. 455–457.
L. Osipow et al., "Micro–Emulsion Process for the Preparation of Sucrose Esters", The Journal of the American Oil Chemists' Society, vol. 44, 1967, pp. 307–309.

G. Rizzi et al., "A Solvent–free Synthesis of Sucrose Polyesters", J. Am. Oil. Chem. Soc., 1978, vol. 55, pp. 398–401.
K. Hess et al., "Kurt Hess and Ernst Messmer: Uber die Synthese von Fettsäure–Derivaten der Zuckerarten", Chem. Ber., vol. 54, 1921, pp. 499–523.
R. O. Feuge et al., "Preparation of Sucrose Esters by Interesterification", J. Am. Oil. Chem. Soc., vol. 47, Feb. 1970, pp. 56–60.
H. Fletcher, Jr., "Benzoates", Methods of Carbohydr. Chem., vol. 2, 1963, pp. 231–233.
R. C. Chalk et al., "Selective Mesylation of Carbohydrates. II. Some Mesyl Esters of Methyl α–and β–D–Glucopyranosides. Methyl α– and β–D–Galactopyranosides, and of Methyl α–D–Mannopyranoside", J. Org. Chem., vol. 31, No. 220, May 1966, pp. 1509–1514.
H. Pfander et al., "The Synthesis of Crocetin–di–(β–D–glucosyl)Ester. A New Method for the Selective Esterification of Unprotected β–D–Glucose", Helv. Chim. Acta, vol. 62, 1979, pp. 1944–1951.
K. Yoshimoto et al., "Regioselective Syntheses of Mono–O–acylglucoses", Chem. Pharm. Bull., 1979, vol. 27, No. 11, pp. 2661–2674.
M. R. Jenner et al., "Use of Dimethoxydiphenylsilane, NN–Dimethylformamide, and Toluene–p–sulphonic Acid as a Novel Acetalating Reagent", J.C.S. Chem. Comm., 1980, pp. 50–51.
F. Dasgupta et al., "Acetylation of carbohydrates by transesterification using ethyl acetate and sodium hydride", Carbohydrate Research, 1983, vol. 114, pp. 153–157.
D. Loganathan et al., "Phase Transfer Catalysed Glycosylation: Part I—Synthesis of 1–O–(p–Methoxy–cinnamoyl)–2,3,4,6–tetra–O–acetyl–β–D–glucopyranose", Indian Journal of Chemistry, vol. 22B, Apr. 1983, pp. 400–401.
D. Plusquellec, et al., "Chimie Des Sucres Sans Groupements Protecteurs—I—Esterification Regioselective De L'Hydroxyle Anomere Du Lactose, Du Maltose Et Du Glucose", 1986, vol. 42, No. 9, pp. 2457–2467.
M. Therisod et al., "Facile Enzymatic Preparation of Monoacylated Sugar in Pyridine", J. Am. Chem. Soc., 1986, vol. 108, No. 18, pp. 5638–5640.
S. Riva et al., "Protease–Catalyzed Regioselective Esterification of Sugars and Related Compounds in Anhydrous Dimethylformamide", Journal of the American Chemical Society, 1988, vol. 110, pp. 584–589.
K. Bock et al., "The Conformational Properties of Sucrose in Aqueous Solution: Intramolecular Hydrogen–Bonding", Carbohydrate Research, 1982, vol. 100, pp. 63–74.
J. C. Christofides et al., "Co–operative and Competitive Hydrogen Bonding in Sucrose determined by SIMPLE H.N.M.R. Spectroscopy", J. Chem. Soc., Chem. Commun., 1985, pp. 1533–1534.

(List continued on next page.)

*Primary Examiner*—Elli Peselev
(74) *Attorney, Agent, or Firm*—McDermott, Will & Emery

(57) ABSTRACT

The invention relates to the synthesis of sulfonated sucrose compounds, surfactants and intermediate cyclic sulfates.

41 Claims, 5 Drawing Sheets

OTHER PUBLICATIONS

D. B. Davies et al., "Comparison of intramolecular hydrogen–bonding conformations of sucrose–containing oligosaccharides in solution and the solid state", Carbohydrate Research, 1987, vol. 163, pp. 269–274.

Vlahov, et al., Journal of Carbohydrate Chemistry, vol.(#) 16(1), pp. 1–10, "Regioselective Synthesis of Sucrose Monoesters as Surfactants," (1997).

Polat, et al., Journal of Carbohydrate Chemistry, vol.(#) 16(9), pp. 1319–1325, Enzyme Catalyzed Regioselective Synthesis of Sucrose Fatty Acid Ester Surfactants, (1997).

Gourlain, et al., Carbohydrate Letters, vol. 2, pp. 143–148, "Regioselective Synthesis of 6–O–Alkyl and Disaccharides Derivatives of Mannofuranose via a 5,6–Cyclic Sulfate," (1996).

Bazin, et al., Carbohydrate Research, vol. 309, pp. 189–205, "Synthesis of Sucrose–Based Surfactants Through Regioselective Sulfonation of Acylsucrose and the Nucleophilic Opening of a Sucrose Cyclic Sulfate," (1998).

(a) DMP (12 equiv), p-TsOH (cat.), DMF, RT, 2 h; (b) Ac₂O, pyr., RT, 12 h; (c) 60% AcOH, 80 °C, 10 min; (d) SOCl₂ (1.5 x 1.05 equiv), pyr (1.5 x 2.05 equiv), EtOAc, RT, 1.5 h; (e) RuCl₃ (cat.), NaIO₄ (2 equiv), CH₃CN:H₂O (1.0:1.5), RT, 1 h; (f) NEt₃ (1.1 equiv), CH₃OH, RT, 12 h; (g) SOCl₂ (1.5 x 1.05 equiv), pyr (1.5 x 2.05 equiv), DMF:EtOAc (1:1), RT, 1.5 h (a) CH₃(CH₂)nCO₂H (1.2equiv), K₂CO₃(1.2equiv), DMF, 80° C, 2 h; (b) CH₃(CH₂)nNH₂, DMF, 80° C, 20 h This is a replacement for Figure 5 in the body of the patent.

SUCROSE BASED SURFACTANTS AND METHODS THEREOF

RELATED APPLICATIONS

This application claims priority from U.S. Provisional Application No. 60/086,756, filed May 27, 1998, which is incorporated herein by reference.

FIELD OF THE INVENTION

The present invention lies in the art of surfactants and more specifically is directed to sucrose-based surfactants. In particular, the invention relates to the synthesis of anionic and amphoteric sucrose-based surfactants by direct sulfonation.

BACKGROUND OF THE INVENTION

The regioselective synthesis of sucrose monoesters of fatty acids including lauryl, myristyl, palmityl and stearyl has been reported. Chemical acylation, using a dibutylstannylene complex, affords 6-O-acylsucrose with 3-O-acylsucrose as minor product. Enzymatic acylation of sucrose, using subtilsin, affords 1'-O-acylsucrose and 1',6'-di-O-acylsucrose as a minor product. These acylsucrose derivatives display better critical micellar concentration (CMC) values than the commercial nonionic surfactants. The CMC value is the specific concentration in aqueous solution at which the molecules aggregate in micelles. However, the stearyl derivatives, having the longest fatty chain and expected to display the best CMC values, are water insoluble. The inventors have found that the regioselective introduction of a polar sulfate group into these acyl derivatives improves their water solubility as well as their CMC values.

The direct regioselective synthesis of O-acyl, O-sulfosucrose derivatives can be achieved by regioselective sulfonation of sucrose followed by regioselective acylation, or by regioselective acylation followed by regioselective sulfonation. Introduction of O-sulfo groups is usually done by directly treating hydroxyl groups with a common sulfonation reagent, including complexes of sulfur trioxide and Lewis base, such as N,N-dimethylformamide (DMF), pyridine or trialkylamine. Other sulfonation reagents include sulfuric acid in presence of N,N'-dicyclohexylcarbodiimide or acetic anhydride, piperidine-N-sulfonic acid, and chlorosulfonic acid. The regioselective sulfonation of partially protected monosaccharides and disaccharides proceeds similarly to O-acylation. Sulfonation of the primary position is preferred and the reaction progresses with the formation of isomeric primary monosulfates followed by sulfonation of secondary hydroxyl groups. Dibutylstannanediyl acetals can also be used for the regioselective sulfonation of partially protected monosaccharides and disaccharides using sulfur trioxide-triethylamine complex.

An O-sulfo group can also be introduced regiospecifically by performing the nucleophilic opening of a cyclic sulfate, this method being useful for both regiospecific introduction of nucleophile and sulfo groups. These nucleophilic reactions have high reactivity and the wide variety of available O-nucleophiles (phenolate, amine oxides or benzoate), S-nucleophiles (thiocyanate, thiophenolate), halide nucleophiles (tetraethyl or tetrabutyl ammonium fluoride or chloride), C-nucleophiles (Grignard Reagents, phenyllithium, sodium phenylacetylide), and N-nucleophiles (azide and amines). No cyclic sulfate synthesis of unprotected carbohydrates, if particular of sucrose, are known. However, the expected regiospecific opening of a cyclic sulfate makes this approach a very attractive and a potentially powerful way for the regiospecific synthesis of mono-O-sulfosucrose derivatives. Moreover, the use of a nucleophile having a fatty chain might lead to new types of surfactants, in which both hydrophobic and sulfate moities are regiospecifically introduced.

Attempts to synthesize cyclic sulfates of unprotected sugars with sulfuryl chloride and pyridine have been reported. However, the reaction has never been clean and several side products were isolated. For example, reaction of sucrose with sulfuryl chloride at −78° C. affords the 6,6'-dichloro-6,6'-deoxysucrose and 6'-chloro-6'-deoxysucrose in 43% and 29% yield. At room temperature, a complex mixture is formed from which 3',4'-anhydro-1',6'-dichloro-1',6'-dideoxy-β-D-ribo-hexulo-furanoside 2,3-cyclic sulfate is isolated in 17% yield, showing that chlorination occurs as well as inversion of configuration during cyclic sulfate formation. Thus, the reaction of sulfuryl chloride with carbohydrates containing free hydroxyl groups has become a well established method for the preparation of chlorodeoxysugars. The conversion of a vicinal cis diol system to a cyclic sulfate in protected carbohydrates is readily accomplished with sulfuryl chloride. By using $SO_2Cl_2$, the methyl 4,6-O-benzilidene-β-D-mannopyranoside 2,3-cyclic sulfate, and 1,6-anhydro-4-O-benzyl-β-D-mannopyranoside 2,3-cyclic sulfate [28] were obtained in 60% and 85% yield.

The reaction of diols with thionyl chloride ($SOCl_2$) in the presence of an amino base gives cyclic sulfites directly and in good yield, unlike the analogous reaction with sulfuryl chloride ($SO_2Cl_2$) which usually results in only very low yields of the corresponding cyclic sulfates. The ring strain energy (~5–6 kcal/mol) of 1,2 cyclic sulfates is most often cited as the reason of the very poor yields in their direct preparation from a diol and $SO_2Cl_2$ (or $SO_2X_2$).

Cyclic sulfates are readily prepared through the oxidation of cyclic sulfites. Permanganate oxidation of the sulfite was originally the favored route to cyclic sulfates. It has been reported that the oxidation step was much cleaner when effected by a stoichiometric amount of ruthenium(IV) tetraoxide ($RuO_4$). Gao and Sharpless reported the use of a catalytic amount of ruthenium(III) trichloride ($RuCl_3$) with $NaIO_4$ as a preparative method for the synthesis of cyclic sulfates from cyclic sulfites. Various syntheses of cyclic sulfates of mannitol and mannosides, using this method, reportedly gave good yields.

Another approach for the synthesis of cyclic sulfites and sulfates from protected carbohydrates relies on the use of N,N'-thionyldiimidazole or N,N'-sulfuryldiimidazole, respectively. However, this chemistry requires the use of a strong base, such as NaH. Phenyl chlorosulfate has also been reported to give the corresponding cyclic sulfate of protected sugars in 60–70% yield. Only 1,2-cyclic sulfites of the unprotected carbohydrates, glucose, galactose and mannose have been synthesized using N,N'-thionylimidazole. These cyclic sulfites were reportedly unstable and were used in situ in the reaction with azide. Schmidt et al. recently reported the use of cyclic sulfate to prepare sugar-based surfactants. However, the cyclic sulfates synthesized from 1,2-fatty diols, were used for alkylation of glucose to obtain anomeric alkyl glycosides.

The regioselective introduction of fatty acyl groups into sucrose, either chemically or enzymatically, leads to surface active neutral sucrose esters. The synthesis of new sulfated surfactants in the present invention demonstrates the regioselective sulfonation of O-acylsucrose derivatives and the nucleophilic opening of an intermediate cyclic sulfate to prepare anionic and amphoteric sucrose-based surfactants.

SUMMARY OF THE INVENTION

It is accordingly an aspect of the invention to provide methods for producing anionic and amphoteric sucrose-based surfactants and sulfonated sucrose structures.

It is another aspect of the invention to provide such sucrose-based surfactants and sulfonated sucrose structures, as well as intermediate cyclic sulfate and sulfite structures.

BRIEF DESCRIPTION OF THE DRAWINGS

For a full understanding of the invention, the following detailed description should be read in conjunction with the drawings, wherein.

DETAILED DESCRIPTION OF THE PREFERRED EMBODIMENTS

Figure 1:
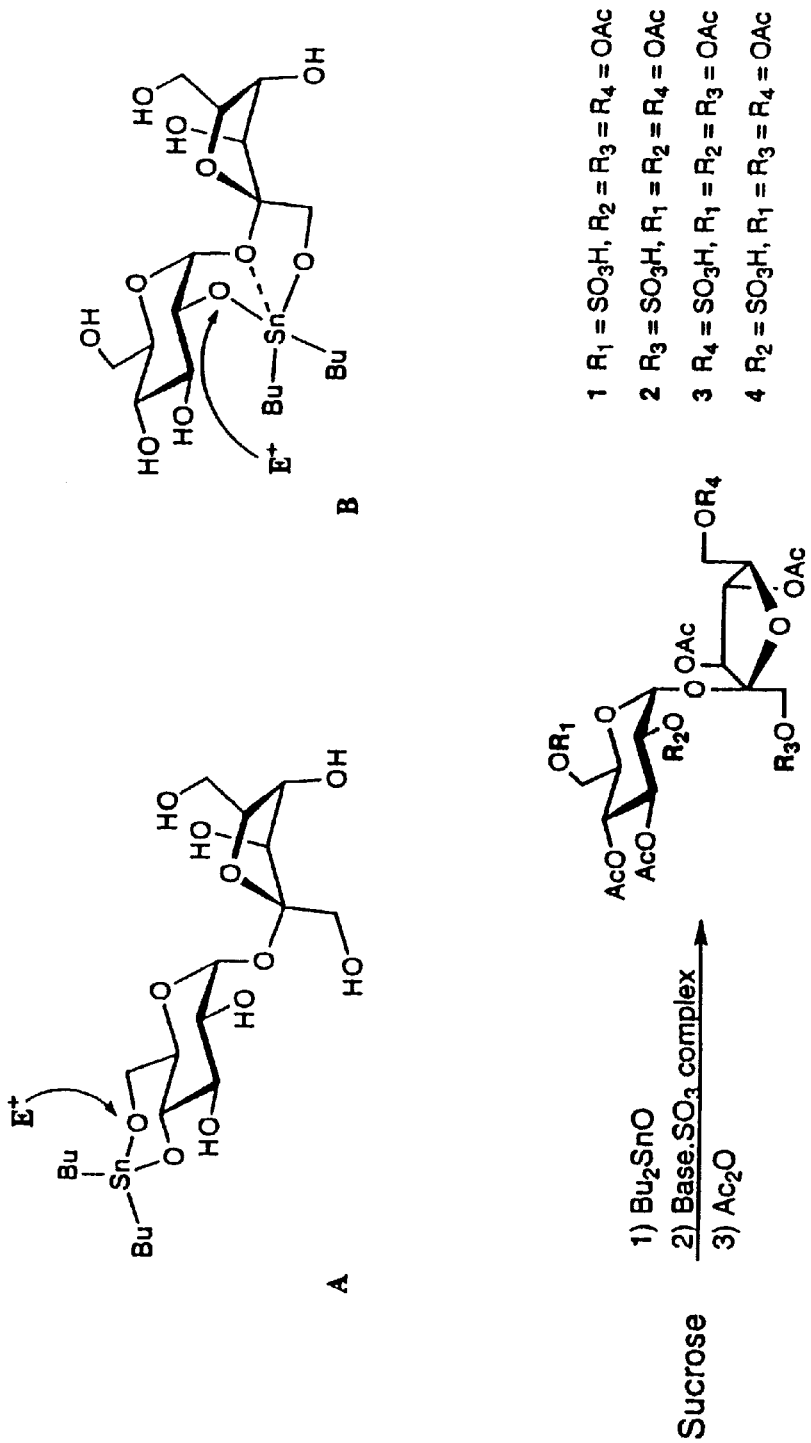
FIG. 1 is a reaction scheme for the sulfonation of sucros-stannylene complex with sulfur trioxide complexes.

Synthesis of a new class of anionic and amphoteric sucrose-based surfactants is disclosed. Direct sulfonation of 6-O-acylsucrose using pyridine-sulfur trioxide complex leads to a mixture of the regioisomeric monosulfates, 6-O-acyl-4'-O-sulfosucrose and 6-O-acyl-1'-O-sulfosucrose, while sulfonation of 1'-O-acylsucrose afforded a mixture of 1'-O-acyl-6'-O-sulfosucrose and 1'-O-acyl-6-O-sulfosucrose. The ratio of regioisomers ranged from 4.7:1.0 to 7.5:1.0, depending on reaction time and the size of the fatty acyl chain. The regiospecific synthesis of 6-O-acyl-4-O-sulfosucrose derivatives was accomplished by nucleophilic substitution of the sucrose 4,6-cyclic sulfate using various fatty acids. The amphoteric 6-alkylamino-6-deoxy-4-O-sulfosucrose surfactants were also synthesized by nucleophilic substitution of the sucrose cyclic sulfate by different fatty amines. All the newly synthesized sucrose-based surfactants displayed excellent surface active properties.

Examples of sulfonated sucrose structures are those having the structure of claim 1 wherein $R_1$ to $R_4$ may be the same or different and can be —SO$_3$H, —OAc, an ether or ester having from one to ten carbon atoms, preferably two to six carbon atoms or a silyl having from one to four silicon atoms, preferably one to three silicon atoms.

Further examples of sulfonated sucrose structures are those having the structure of claims 6 and 12 wherein $R_1$ may be a substituted benzoyl in which the substituents are halo, such as fluoro, chloro or bromo, alkyl having from one to five carbon atoms, alkenyl having from two to seven carbon atoms and substituted such alkyl and alkenyl groups in which the substitutions are halo.

Examples of surfactants of the invention are those having the structures of claims 15 and 20 wherein n of the ester group is from 5 to 25, desirably 8 to 20 and preferably 10 to 16.

Further examples of surfactants of the invention are those having the structure of claim 27 wherein n of the ester group and the amine group is from 5 to 25, desirably 8 to 20 and preferably 12 to 18.

Examples of intermediate cyclic sulfates and sulfites of the invention are those having the structure of claim 36 and 37, respectively, wherein R is -Ac, -Bz, Bn or silyl.

Processes for synthesizing a sucrose derivative with a nucleophilic agent may employ a nucleophile which is a fatty acyl or aminoalkyl compound having from 4 to 30 carbon atoms, preferably 14 to 20 carbon atoms.

Regioselective sulfonation of sucrose.—The regioselective sulfonation of sucrose was initially attempted by reacting the dibutylstannylenesucrose complex with various sulfur trioxide complexes including, Pyr.SO$_3$, NMe$_3$.SO$_3$ and DMF.SO$_3$ complexes. The sucrose-stannylene complex was formed by refluxing sucrose and dibutyltin oxide in methanol for 3 h, followed by evaporation of the methanol. The resulting complex was then dissolved in anhydrous DMF and treated at 25° C. with 1.0 equivalent of sulfonating agent, with reaction time varying from 5 h (Pyr.SO$_3$) to 24 h (NMe$_3$.SO$_3$, DMF.SO$_3$). The resulting O-sulfosucrose derivatives were acetylated to determine their sulfonation pattern by $^1$H-NMR. When using Pyr.SO$_3$, a mixture of the three primary O-sulfo derivatives were obtained without any marked regioselectivity, as demonstrated by the ratio 6-O-sulfo- (1):1'-O-sulfo- (2):6'-O-sulfo- (3) sucrose of 1.9:1.4:1.0. See FIG. 1. In the following description, numerals 1–32 refer to specific compounds as shown in the figures. A lower temperature (4° C.) did not enhance the regioselectivity giving a ratio of 1:2:3 of 1.5:1.4:1.0. The use of DMF.SO$_3$ led to a mixture of 6-O-sulfo- and 6'-O-sulfosucrose 1 and 3 with a limited regioselectivity of 1.2:1.0. The regioselectivity of this reaction, as well as the regioselective formation of 6-O-acyl derivatives during acylation of sucrose-stannylene complex, is different from that observed for the formation of the 2-O-esters of some other α-D-hexopyranosides. This sulfonation pattern obtained suggests that sucrose has formed preferred six-membered stannylene acetal intermediate A, affording, upon reaction with sulfur trioxide complex, an electrophilic substitution at the primary C-6 position. Surprisingly, sulfonation of sucrose-stannylene complex using NMe$_3$.SO$_3$, after acetylation, led to a mixture of 1'3,3',4,4',6,6'-hepta-O-acetyl-2-O-sulfosucrose (4, 68%) and 2,3,3',4,4',6,6'-hepta-O-acetyl-1'-O-sulfosucrose (2, 11%) (FIG. 1). The 6-O-sulfosucrose, which was expected to be the major sulfonation product, was not detected. When the same reaction was performed on uncomplexed sucrose, a mixture of 6-, 1'- and 6'-O-sulfosucrose derivatives 1, 2 and 3 was obtained in a ratio of 1.9:1.4:1.2. This different sulfonation pattern implies that the five-membered cyclic dibutylstannylene acetal B involving both the C-2 and C-1'hydroxyls of the glucopyranoside and fructofuranoside moieties as well as the anomeric oxygen was formed, leading to an electrophilic substitution at the C-2 position in the five-membered stannylene complex B.

The difference of regioselectivity observed when using different sulfur trioxide complexes suggests that both six-membered and five-membered ring stannylene complexes A and B are formed with sucrose, enhancing the nucleophicity of both C-6 and C-2 hydroxyls of the glucopyranoside moiety. The fact that the electrophilic substitution occurs preferentially at the C-6 position with Pyr.SO$_3$ and DMF.SO$_3$ and at the C-2 position with NMe$_3$.SO$_3$ seems to demonstrate that electrophilic substitutions on the sucrose-stannylene complex are governed by both the base and the nature and structure of the electrophile.

Regioselective sulfonation of 6-O-benzoylsucrose.—The 6-O-benzoylsucrose [42] was first studied as a model compound for O-acyl fatty esters of sucrose. Capillary electrophoresis (CE) was used to monitor the sulfonation reactions and to determine the ratio of benzoylsucrose, mono- and di-O-sulfo products. Our group has described the use of CE as an analytical tool for monitoring the sulfonation of O-benzyl sugars. The sulfonation pattern was determined by $^1$H NMR spectroscopy after acetylation of the reaction mixture and purification of the acetylated monosulfate sucrose derivatives. The sulfonation reaction was first performed in anhydrous DMF by adding 1 equiv. of Pyr.SO$_3$ complex to a solution of 6-O-benzoylsucrose. The CE data showed that the sulfonation occurred largely in the first 15 min and that a longer reaction time did not increase the conversion of starting material. To improve this conversion, the sulfonation reaction was next performed by adding 1 equiv. of sulfonating agent three times at 15-min intervals (Pyr.SO$_3$) or three times at 1.5-h intervals (NMe$_3$.SO$_3$ and DMF.SO$_3$). An aliquot of the reaction mixture was removed 15 min after each addition and analyzed by CE, and the ratios of mono- and di-O-sulfo derivatives were determined (Table 1). These results show that: 1. Pyr.SO$_3$ afforded faster sulfonation of 6-O-benzoylsucrose, the ratio 6-O-benzoylsucrose:mono-O-sulfo:di-O-sulfo derivatives of 1.9:1.0:0.2 being reached in 15 min with Pyr.SO$_3$, compared to 1 h with NMe$_3$.SO$_3$ and DMF.SO$_3$; 2. DMF.SO$_3$ afforded the best conversion of 6-O-benzoylsucrose to mono-O-sulfo product with little formation of di-O-sulfo product, but required longer reaction time; and 3. For both NMe$_3$.SO$_3$ and Pyr.SO$_3$, the conversion of 6-O-benzoylsucrose should not exceed 50% in order to keep a ratio mono-:di-O-sulfo derivatives greater than 1.0:1.0.

Figure 2:
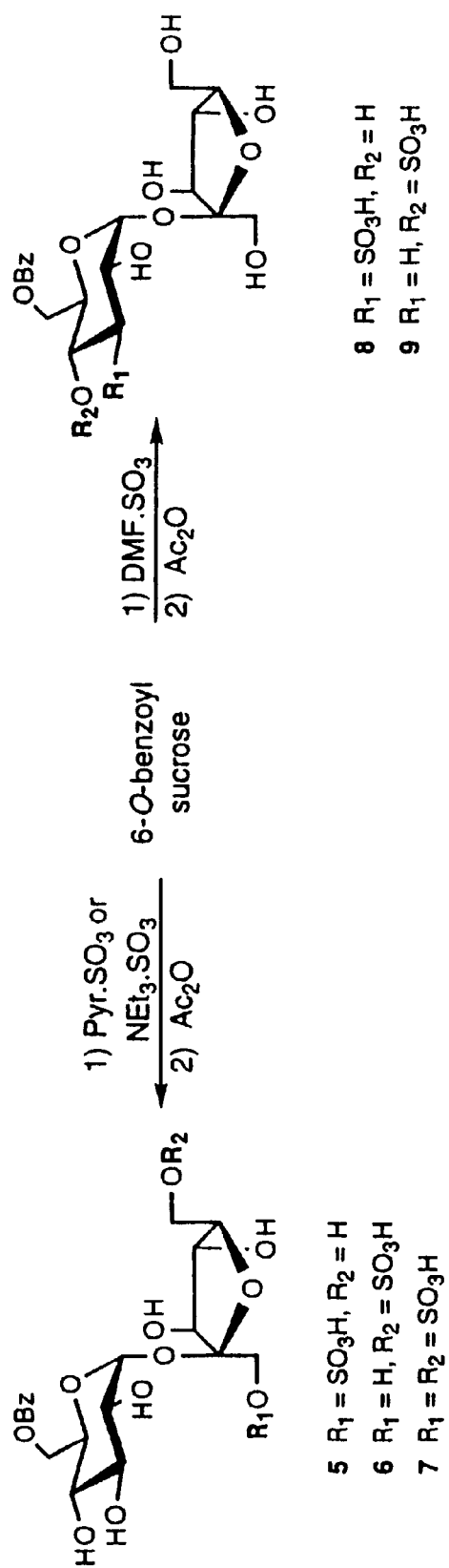
FIG. 2 is a reaction scheme for the sulfonation of 6-O-benzoylsucrose with sulfur trioxide complexes.

Sulfonation using Pyr.SO$_3$ and NMe3.SO$_3$ occurred as expected at the primary hydroxyls 1' and 6' but with limited regioselectivity (FIG. 2). A mixture of 2,3,3',4,4',6'-hexa-O-acetyl-6-O-benzoyl-1'-O-sulfosucrose 5 and 1',2,3,3',4,4'-hexa-O-acetyl-6-O-benzoyl-6'-O-sulfosucrose 6 with a ratio of 1.0:1.2 was obtained in both cases. Regioselectivity was slightly improved from 1.0:1.2 to 1.0:1.6 when the sulfonation with Pyr.SO$_3$ was performed at reduced temperature (4° C.). In these reactions, the 2,3,3',4,4'-penta-O-acetyl-6-O-benzoyl-1', 6'-di-O-sulfosucrose 7 was also isolated in lower yield. Surprisingly, sulfonation of the 6-O-benzoylsucrose with DMF.SO$_3$ led to a mixture of 1',2,3',4,4',6'-hexa-O-acetyl-6-O-benzoyl-3-O-sulfosucrose 8 and 1',2,3,3',4',6'-hexa-O-acetyl-6-O-benzoyl-4-O-sulfosucrose 9 in a ratio of 1.2:1.0. Since Pyr.SO$_3$ gave the fastest sulfonation and the best product ratios, this sulfonation reagent was selected for further studies.

Figure 3A:
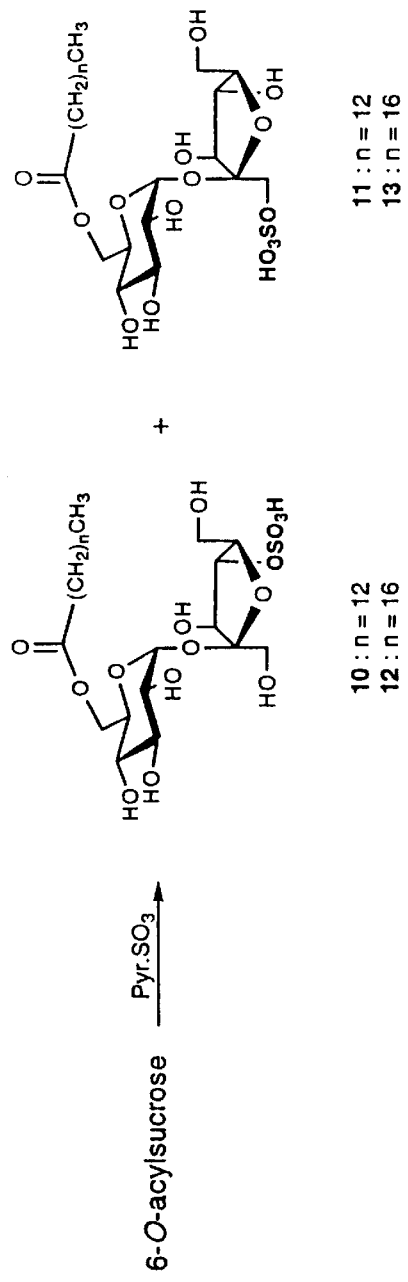
FIG. 3A and FIG. 3B is a reaction scheme for the sulfonation of 6-O-acyl and 1'-O-acylsucrose with Pyr.SO$_3$ complex.
Figure 3B:
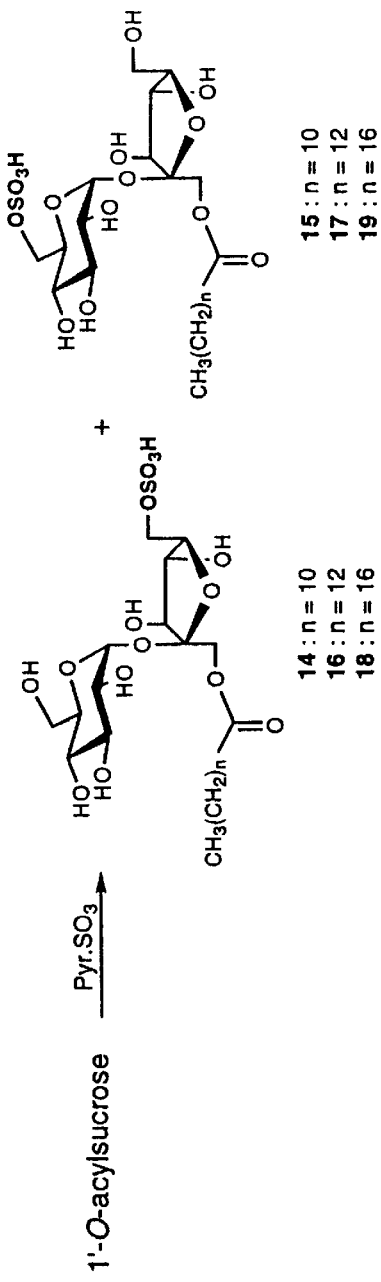

Regioselective sulfonation of 6-O-acylsucrose and 1'-O-acylsucrose.—Sulfonation of 6-O-acylsucrose and 1'-O-acylsucrose derivatives was next examined using Pyr.SO$_3$ complex under various reaction conditions. First, sulfonation of 6-O-myristylsucrose was attempted in pyridine by adding 1 equiv. of Pyr.SO$_3$ complex at three 15-min intervals. The 6-O-myristyl-4'-O-sulfosucrose 10 and 6-O-myristyl-1'-O-sulfosucrose 12 were obtained in 25% and 2% yield, respectively (FIG. 3, Table 2). The 4'-O-sulfo group in 10 was unambiguously determined by $^1$H NMR spectroscopy after acetylation of 10. When the same reaction was performed by adding 1 equiv. of Pyr.SO$_3$ complex two times at 15-min intervals and 1 more equiv. at 12 h, the conversion of 6-O-myristylsucrose was higher, and the mono-O-sulfo derivatives 10 and 11 were obtained in 70% and 10% respectively (Table 2). If the reaction was run for 48 h after addition of the last equivalent of Pyr.SO$_3$ complex, the overall yield was improved from 80% to 91%, however, the regioselectivity was reduced from 7.0:1.0 to 1.6:1.0. The same results were observed for 6-0-laurylsucrose and 6-O-stearylsucrose (Table 2). The sulfonation of 1'-O-acylsucrose derivatives was performed in the same reaction conditions and led, in every case, to the formation of 1'-O-acyl-6'-O-sulfosucrose as major products and 1'-O-acyl-6-O-sulfosucrose as minor products, the yields and regioselectivity ratios being similar to those for the sulfonation of 6-O-acylsucrose derivatives (Table 2).

These results show that the presence of a long acyl chain induced a good regioselectivity during the sulfonation of acylsucrose. As expected, the sulfonation of 1'-O-acylsucrose derivatives occurred at the primary C-6' and C-6 hydroxyls. However, sulfonation of 6-O-acylsucrose derivatives occurred primarily at the secondary C-4' hydroxyl and at the primary C-1' hydroxyl.

Figure 4:
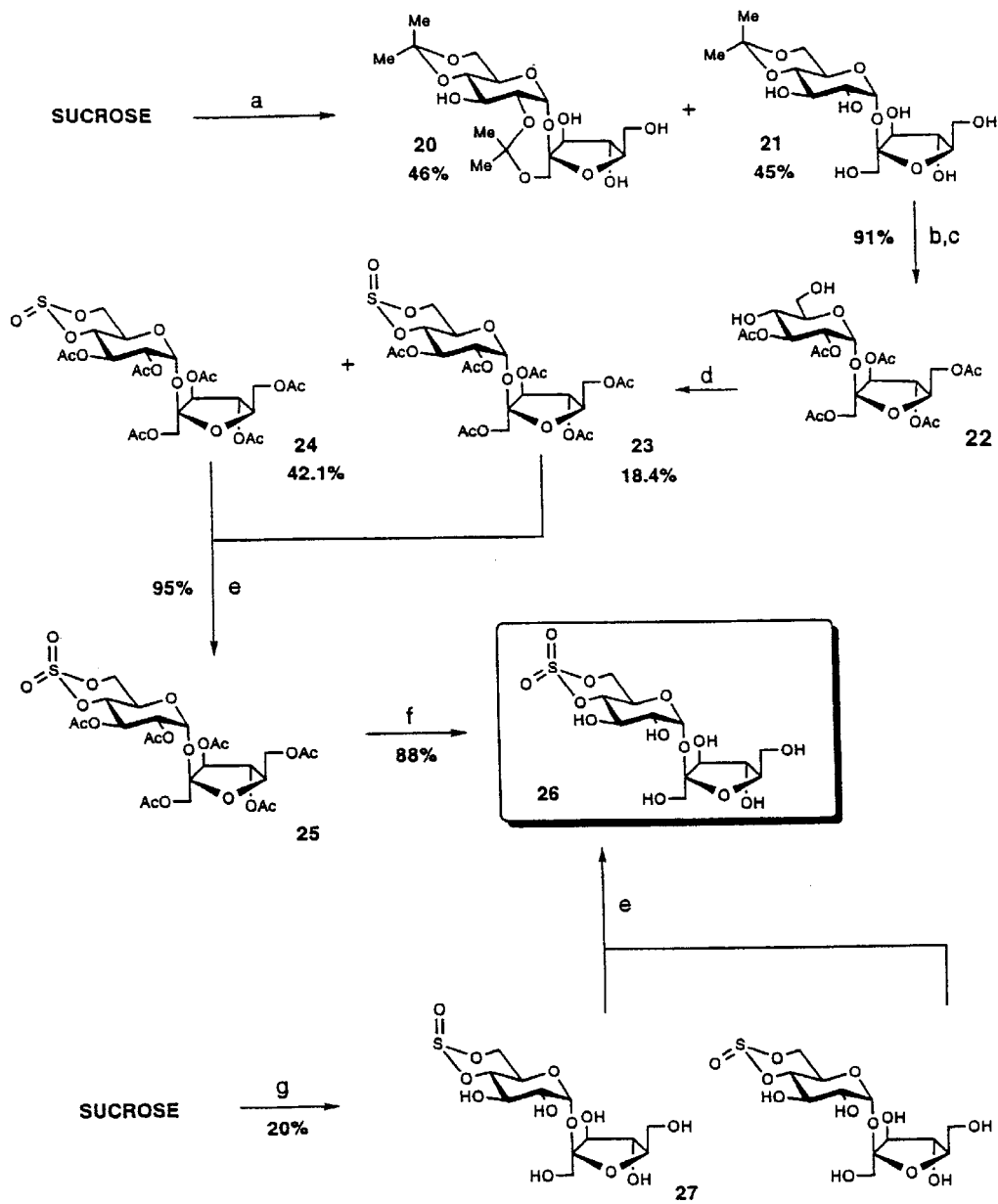
FIG. 4 is a reaction scheme for the synthesis of sucrose 4,6-cyclic sulfate.

Synthesis of sucrose cyclic sulfate.—The synthesis of the cyclic sulfite of unprotected sucrose was first attempted using thionyl chloride (SOCl$_2$) under a variety of conditions. When sucrose was reacted in DMF with SOCl$_2$ (1.05 equiv.) and pyridine (2.1 equiv.) at room temperature, the formation of a major compound having a polarity similar to sucrose was observed by TLC. The $^1$H NMR spectrum of this derivative, purified by flash chromatography (113 mg from 100 mg sucrose), showed a downfield shift for H-3'(Δδ~0.2 ppm) and upfield shifts for H-1'a,b (Δδ~0.2 ppm), H-4' (Δδ~0.7 ppm), and one H-6' (Δδ~0.2 ppm). Protons attached to carbons involved in a cyclic sulfite are known to be shifted downfield. Thus, the isolated compound was not a cyclic sulfite and no further characterization of this product was performed. When the same reaction was performed in 1:1 DMF-CH$_2$Cl$_2$, an orange gel-like suspension was formed, and no product could be isolated. Next, reaction conditions were chosen which were as close as possible to those described in the literature, i.e. using protected sucrose and ethyl acetate solvent. The 1',2,3,3',4',6'-hexa-O-acetylsucrose 22 was first synthesized using standard methods (FIG. 4). Isopropylidenation of sucrose using 2,2'-dimethoxypropane (DMP) led to a mixture of 1',2:4,6-di-O-isopropylidenesucrose 20 and 4,6-mono-O-isopropylidenesucrose 21 in 46% and 45% yield, respectively. Peracetylation of 22 followed by deacetalation using acetic acid afforded the 4,6-free diol 22 in 91% yield. The corresponding cyclic sulfites 22 and 23 were obtained by reacting 22 with SOCl$_2$ and pyridine in ethyl acetate and at room temperature for 1.5 h. An excess of thionyl chloride (1.05 equiv. followed after 45 min by 0.5 equiv.) was required for the complete conversion of 22. The two new compounds observed by TLC were isolated, purified by silica gel chromatography and characterized. Fast-atom-bombardment mass spectrometry (FABMS) analysis of both compounds 23 and 24 showed a molecular ion peak [M+Na]$^+$ of 663, consistent with the molecular formula of the cyclic sulfite, suggesting that they were diastereomers. The structure of the cyclic sulfites 23 and 24 were confirmed by $^1$H NMR spectroscopy. From NMR spectroscopy it was also possible to determine the configuration of the sulfoxide group. The significant deshielding of protons that are syn-axial to an axial sulfoxide group can be used to assign the configuration at the S→O center. For 23, the chemical shifts of H-4 and one of the H-6 are significantly deshielded, compared to the free diol 22 (Δδ=1.12 ppm for H-4 and Δδ=0.76 ppm for H-6). From these observations it appeared that the sulfoxide group in 23 adopts an axial configuration. For 24, the chemical shifts of H-5 and one of the H-6 are largely deshielded (AΔδ=0.74 ppm for both), but H-4 is considerably less deshielded than in 23 (AΔδ=0.45 ppm). These observations are in accordance with the equatorial configuration of the sulfoxide in 24. This reaction was repeated with different bases and at different temperatures, and the resulting overall yields ranged from 34% to 61% (Table 3). For a given base, the yields in cyclic sulfites 23 and 24 were 10 to 20% higher when the reaction was performed at room temperature than at 0° C. (Table 3). These results also show that the formation of the axial sulfite 23 was favored by a lower reaction temperature and by the presence of triethylamine. It should be noted that at the end of each reaction the pH of the reaction mixture was acidic (pH 2–3), which could explain the relatively modest yields obtained. When the same reaction was performed with an excess of pyridine to neutralize this acidity, the axial cyclic sulfite 23 became the predominant product, but the resulting overall yield did not increase. This could result from a partial hydrolysis of the cyclic sulfite, which is known to occur at pH>7. N,N'-thionyldiimidazole was also used in an effort to avoid the formation of acid during the reaction, but no improvement in yield was obtained (Table 3).

Cyclic sulfites 23 and 24 were oxidized using a catalytic amount of $RuCl_3$ with a stochiometric amount of sodium periodate ($NaIO_4$) in a mixture of acetonitrile and water (1.0:1.5). The cyclic sulfate 25 was readily obtained in excellent yield (95%). Deacetylation of 25 in standard conditions (triethylamine and methanol) led to the corresponding cyclic sulfate 26 in 88% yield. The cyclic sulfate was stable under deacetylation conditions, while the cyclic sulfite was not.

Next, the same reaction was performed on unprotected sucrose in a mixture of 1:1 DMF-ethyl acetate, using $SOCl_2$ (1.5×1.05 equiv.) and pyridine (1.5×2.10 equiv.). After 2 hours, the 4,6-cyclic sulfite 27 was isolated in 20% yield. Some glucose derivatives were also obtained, indicating that hydrolysis of the glycosidic bound occurred under the reaction conditions. Unfortunately, catalytic oxidation of the cyclic sulfite only afforded trace amounts of the cyclic sulfate by TLC. The presence of free hydroxyls might have been responsible for the loss of catalyst activity of ruthenium tetroxide.

Figure 5:
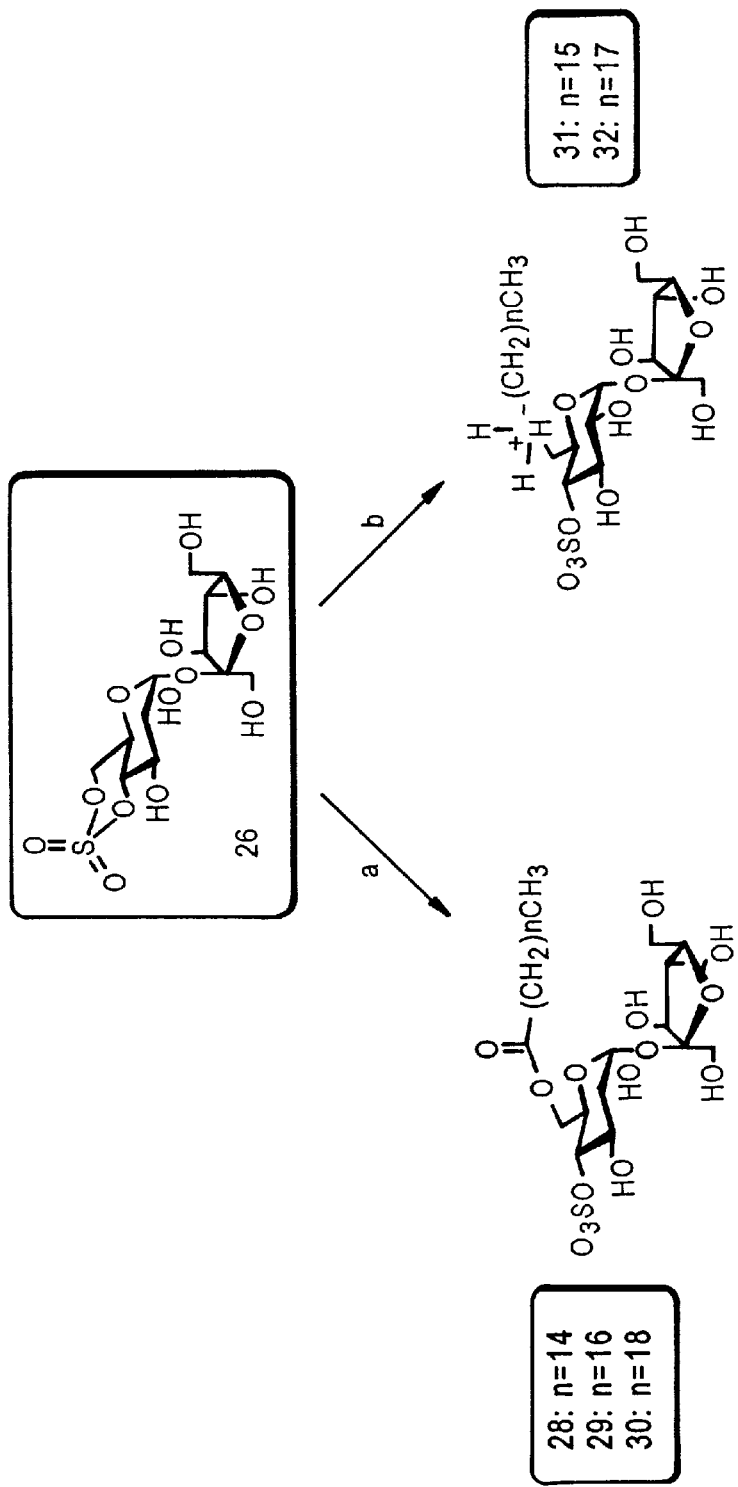
FIG. 5 is a reaction scheme for the nucleophilic opening of sucrose-4,6-cyclic sulfate by O- and N-nucleophiles.

Cyclic sulfate opening with O-nucleophile.—Once the sucrose cyclic sulfate had been synthesized, we focused our attention on the nucleophilic opening of the cyclic sulfate using O-nucleophiles (palmitic, stearic and eicosanoic acids) and N-nucleophiles (hexadecylamine and octadecylamine), as shown in Scheme 5. When cyclic sulfate 26 was reacted at room temperature in DMF with a slight excess (1.2 equiv.) of palmitic acid and potassium bicarbonate, no reaction occurred. However, when heated at 80° C. for 3 h, the 6-O-palmityl-4-O-sulfosucrose 28 was regiospecifically obtained in 75% yield. The 4-position of O-sulfonation was confirmed by acid catalyzed hydrolysis of 28. The $^1$H NMR spectrum of the resulting compound showed that the chemical shift of H-4 was largely deshielded (Δδ=−0.95 ppm) while the H-5, H-6a and H-6b chemical shifts were moderately shielded (Δδ=+0.1a, −0.30 and +0.10 ppm, respectively). The same reaction, performed with stearic acid and eicosanoic acid under identical conditions, led to the 6-O-stearyl-4-O-sulfosucrose 29 and 6-O-eicosanoyl-4-O-sulfosucrose 30 in 72% and 70% yield, respectively (FIG. 5).

Cyclic sulfate opening with N-nucleophile.—Reaction of the sucrose cyclic sulfate 28 with a slight excess of hexadecylamine or octadecylamine in DMF, at 80° C. for 17 h led to the corresponding amphoteric 6-deoxy-6-hexadecylamino-4-O-sulfosucrose 33 and 6-deoxy-6-octadecylamino-4-O-sulfosucrose 34 in 76% and 60% yield, respectively.

Surface activity of O-acyl-O-sulfosucrose derivatives.—All the new synthesized O-acyl-O-sulfosucrose derivatives displayed surface-active properties (Table 2). This CMC value is of practical importance since it is the minimal concentration of surfactant required to solubilize hydrophobic molecules in water. Our laboratory recently demonstrated that a calorimetric method for CMC determination was useful for the accurate analysis of sucrose-based surfactants. This dye solubilization method was used to determine the CMC of the sulfated sucrose surfactants.

The CMC values measured for the 6- and 1'-O-acylsucrose derivatives were more than an order of magnitude lower than that of commercially prepared ionic and nonionic surfactants (Table 2). As expected, the CMC values decrease with longer acyl chain. The introduction of an O-sulfo group into these O-acylsucrose derivatives led to improved surface activity, resulting in CMC values of 1 to 2 orders of magnitude lower than the corresponding O-acylsucrose derivatives, the O-stearyl-O-sulfosucrose derivatives 12, 13, 29 displayed exceptionally low CMC values while the O-eicosanoyl-O-sulfosucrose 31 was insufficiently soluble in water to determine its CMC value. The 6-O-hexadecylamino-4-0-sulfosucrose derivative 31 also has a very low CMC value, making this amphoteric sufactant a very attractive target for further study. At a given acyl chain size, the 1'-O-acyl monoesters and their O-sulfo derivatives show slightly lower CMC values than the corresponding 6-O-acyl derivatives. In both 1'-O-acyl and 6-O-acyl series, the different sulfonation position 6'/6 or 4'/1', respectively, does not affect the CMC value. However, the 6-O-stearyl-4-O-sulfosucrose 29 displays a CMC value 3-times higher than the 6-O-stearyl-4'-O-sulfosucrose 12 and 6-O-stearyl-1'-O-sulfosucrose 13. These difference in surface activity could be the result of the relative position of both acyl chain and sulfate group. In aqueous solution, these anionic surfactants lead to micelles in which the hydrophobic acyl chains constitute the interior of the micelle, while the hydroxyl and sulfo groups are localized on the external surface of the micelle. These structures are easier to form if the acyl chain and sulfo group are far apart from each other. The proximity of the 6-O-acyl chain and the 4-O-sulfo group in 29 could then explain this increase of CMC value.

Conclusions

New O-acyl-O-sulfosucrose-based surfactants have been synthesized using two different approaches. The first one, involving the direct sulfonation of fatty O-acylsucrose, occurs regioselectively at the 4'- and 1'- positions for the 6-O-acylsucrose derivatives and at the 6'- and 6-positions for the 1'-O-acylsucrose derivatives. The best yields, 77% to 85%, and regioselectivities, 4.7:1.0 to 7.5: 1.0, were obtained by adding 1 equiv. of the $Pyr.SO_3$ three times at 15-min intervals with a 12-h reaction time. A second approach was also described that involved the regiospecific nucleophilic opening of an intermediate sucrose 4,6-cyclic sulfate. Ring opening with fatty acids led to anionic sucrose based surfactants in 70–75% yield, having the fatty acyl chain and the sulfate group in the 6- and 4-position, respectively, while amphoteric 6-deoxy-6-alkylamino-4-O-sulfosucrose surfactants were obtained in 60–76% yield using fatty amines.

All these new anionic and amphoteric sucrose based-surfactants display exceptional surface active properties with CMC values from two to three orders of magnitude lower than those of commercial anionic surfactants. These new sucrose-based surfactants are prepared using inexpensive renewable starting materials, display very good surface active properties, should be biodegradable and thus, may represent surfactants of potential commercial value.

The following examples illustrate the invention.

Experimental

General Procedures.—Nuclear magnetic resonance ($^1$H NMR) spectra were recorded at 25° C., in deuterated solvent on a Varian Unity 500 MHz spectrometer. Chemical shifts were recorded in ppm (δ) and coupling constants in Hz, relative to tetramethylsilane as internal standard. The $^1$H NMR spectra were fully assigned by the use of single-frequency decoupling. Optical rotations were measured with a Perkin-Elmer 141 polarimeter. CE was performed on a Dionex CE system (Sunnyvale, Calif.) equipped with a variable wavelength detector. All analyses used a fused silica capillary tube (75 μm i.d., 375 μm o.d., and 75 cm long) from Dionex. Operating buffer was 10 mM sodium borate, 50 mM sodium dodecylsulfate adjusted to pH 8.8 with 1 N HCl. Thin-layer chromatography (TLC) was performed using E. Merck plates of silica gel 60 with fluorescent indicator. Visualization was effected by spraying plates with Von's reagent (1.0 g ceric ammonium sulfate and 24.1 g ammonium molybdate in 31 mL sulfuric acid and 470 mL water) followed by heating at 140° C. Flash chromatography was conducted with silica gel (230–430 mesh, E. Merck). Dichloromethane ($CH_2Cl_2$), N,N-dimethylformamide (DMF), ethyl acetate (EtOAc) and pyridine (Pyr) were anhydrous solvents available from Aldrich. The colorimetric CMC determination [52] used uniformly pre-coated plastic balls that were purchased from Pro Chem, Inc. (Rockford, Ill.). The absorption of the dye was measured at 612 nm on Shimadzu UV-60. All the acylsulfosucrose derivatives were hygroscopic, preventing their elemental analysis. The purity and identity of these surfactants were assessed based on the absence of extraneous signals in their $^1$H NMR spectra and on the expected molecular ion by high resolution mass spectrometry.

Regioselective sulfonation of stannylenesucrose complex.—A mixture of sucrose (500 mg, 1.46 mmol), di-n-butyltin oxide (375 mg, 1.50 mmol) and $CH_3OH$ (10 mL) was refluxed for 3 h. The clear solution was evaporated in vacuo to dryness. The resulting white crystals were coevaporated three times with 10 mL of anhydrous toluene. Anhydrous DMF (5 mL) and sulfur trioxide complex (mg, 1.50 mmol) were added under inert gas. The reaction mixture was stirred at room temperature for 5 h with $Pyr.SO_3$ complex or 24 h with $NEt_3.SO_3$ and $DMF.SO_3$ complexes. The reaction mixture was extracted twice with petroleum ether to remove the organotins and evaporated under in vacuo. The residue was dissolved in water and eluted on a resin Dowex-1×2 200-mesh ion exchange ($Cl^-$). The unreacted sucrose was eluted first with water, and the sulfonated products were then eluted with aqueous sodium chloride. This fraction was concentrated by evaporation in vacuo and desalted by elution through a Bio-Gel P-2 column. The resulting sulfonated mixture was acetylated under standard conditions (acetic anhydride and Pyr), and the acetyl sulfosucrose derivatives were purified by chromatography on silica gel (9:1 $CHCl_3$—$CH_3OH$). The acetylated 2-, 6-, 1'- and 6'-O-sulfosucrose 1–4 were not separable. The ratios of the different reaction mixtures were determined by $^1$H NMR.

Direct O-sulfonation of acylsucrose esters.—Acylsucrose (150 mg) was dissolved in 5 mL Pyr at room temperature, under nitrogen. At three 15-min intervals $Pyr.SO_3$ complex (1 equiv.) was added. The reaction mixture was stirred for 12 h (or 48 h) at room temperature, under nitrogen. Solvent was evaporated in vacuo, and the last traces of Pyr were removed by co-evaporation three times with 10 mL portion of toluene. The remaining residue was subjected to flash chromatography (4:1 $CHCl_3$—$CH_3OH$).

Synthesis of 6-O-acyl-4-O-sulfosucrose derivatives.—To a solution of sucrose cyclic sulfate (50 mg, 0.12 mmol) in anhydrous DMF (5 mL) and under nitrogen was added $K_2CO_3$ (1.2 equiv.) and the fatty acid (1.2 equiv.). The reaction mixture was heated at 80° C. for 3 h. After cooling at room temperature, the reaction mixture was filtered through Celite and evaporated in vacuo. Purification by chromatography on silica gel (3:1, $CHCl_3$—$CH_3OH$) afforded the corresponding 6-O-acyl-4-O-sulfosucrose derivative.

Synthesis of 6-O-alkylamino-6-O-deoxy-4-O-sulfosucrose derivatives.—To a solution of cyclic sulfate sucrose (50 mg, 0.12 mmol) in anhydrous DMF (5 mL) and under nitrogen was the fatty amine (1.2 equiv.). The reaction mixture was heated at 80° C. for 17 h. After cooling at room temperature, the reaction mixture was filtered through Celite and evaporated in vacuo. Purification by chromatography on silica gel (3:1 $CHCl_3$—$CH_3OH$) afforded the corresponding 6-O-alkylamino-6-O-deoxy-4-O-sulfosucrose derivatives.

EXAMPLE 1

1',2,3,3',4,4',6'-hepta-O-acetyl-6-O-sulfosucrose (1).—Sulfonation of the sucrose-stannylene complex (sucrose 500 mg) using $Pyr.SO_3$ (24 mg) or $DMF.SO_3$ (23 mg) complexes afforded, after acetylation and purification by chromatography on silica gel, 1 in 47% and 43% yield, respectively. 1 could not be separated from the regioisomeric monosulfates 2 and 3. $^1$H NMR ($CDCl_3$, 500 MHz): δ2.00–2.20 (m, 21 H, 7 C(O)$CH_3$), 4.24–4.36 (m, 7 H, H-1'a, H-1'b, H-5, H-5', H-6b, H-6'a and H-6'b), 4.42–4.46 (m, 1 H, H-6a), 4.94 (1 H, $J_{1,2}$ 3.7 Hz, $J_{2,3}$ 9.9 Hz, H-2), 5.07 (t, 1 H, $J_{3,4}$ and $J_{4,5}$ 9.6 Hz, H-4), 5.42 (t, 1 H, $J_{3',4'}$ and $J_{4',5'}$ 6.6 Hz, H-4), 5.43 (t, 1 H, H-3), 5.45 (d, 1 H, H-3'), 5.62 (d, 1 H, H-1).

EXAMPLE 2

2,3,3',4,4',6,6'-hepta-O-acetyl-1-O-sulfosucrose (2).—Sulfonation of the sucrose-stannylene complex (sucrose 500 mg) using $Pyr.SO_3$ (24 mg) afforded, after acetylation and purification by chromatography on silica gel, 2 in 24% and 11% yield, respectively. 2 could not be separated from the regioisomeric monosulfates 1, and 3. $^1$H NMR ($CDCl_3$, 500 MHz): δ2.00–2.18 (m, 21 H, 7 C(O)$CH_3$), 4.02 (d, 1 H, $J_{1'a,b}$ 12.1 Hz, H-1'b), 4.31–4.35 (d, 1 H, H-1'a), 4.14–4.26 (m, 6 H, H-1'a, H-5', H-6a, H-6b, H-6'a and H-6'b), 4.27–4.31 (m, 1 H, H-5), 4.82 (dd, 1 H, $J_{1,2}$ 3.7 Hz, $J_{2,3}$ 9.9 Hz, H-2), 5.06 (t, 1 H, $J_{3,4}$ and $J_{4,5}$ 9.9 Hz, H-4), 5.42 (m, 2 H, H-3 and H-4'), 5.51 (d, 1 H, $J_{3',4'}$ 6.2 Hz, H-3'), 5.62 (d, 1 H, H-1).

EXAMPLE 3

1',2,3,3',4,4',6-hepta-O-acetyl-6'-O-sulfosucrose (3).—Sulfonation of the sucrose-stannylene complex (sucrose 500 mg) using $Pyr.SO_3$ (24 mg) or $DMF.SO_3$ (23 mg) complexes afforded, after acetylation and purification by chromatography on silica gel, 3 in 34% and 36% yield, respectively. 3 could not be separated from the regioisomeric monosulfates 1 and 2. $^1$H NMR ($CDCl_3$, 500 MHz): δ6 2.00–2.20 (m, 21 H, 7 C(O)$CH_3$), 4.05 (dd, 1 H, $J_{5',6'a}$ 4.5 Hz, $J_{6'a,b}$ 11.8 Hz, H-6'b), 4.12 (m, 1 H, H-6'a), 4.24–4.36 (m, 5 H, H-1'a, H-1'b, H-5, H-5' and H-6b), 4.38 (m, 1 H, H-6a), 4.82 (1 H, $J_{1,2}$ 3.7 Hz, $J_{2,3}$ 9.92 Hz, H-2), 5.06 (t, 1 H, $J_{3,4}$ and $J_{4,5}$ 9.7 Hz, H-4), 5.42 (t, 1 H, H-3), 5.46 (t, 1 H, $J_{3',4'}$ and $J_{4',5'}$ 6.6 Hz, H-4), 5.52 (d, 1 H, H-3'), 5.74 (d, 1 H, H-1).

EXAMPLE 4

1',3,3',4,4',6,6'-hepta-O-acetyl-2-O-sulfosucrose (4).—Sulfonation of the sucrose stannylene complex (sucrose 500 mg) using $NMe_3 \cdot SO_3$ complex (21 mg) afforded, after acetylation and purification by chromatography on silica gel, 4 in 68% yield. 4 could not be separated from the regioisomeric monosulfate 2. $^1H$ NMR ($CDCl_3$, 500 MHz): δ2.03–2.19 (m, 21 H, 7 C(O)$CH_3$), 4.14–4.18 (m, 3 H, H-1'a, H-1'b and H-6'b), 4.20 (m, 1 H, H-5'), 4.22 (d, 1 H, $J_{6a,b}$ 12.1 Hz, H-6b), 4.30 (m, 1 H, H-5), 4.34 (dd, 1 H, $J_{5',6'a}$ 3.8 Hz, $J_{6'a,b}$ 12.1 Hzm H-6'a), 4.43 (d, 1 H, H-6a), 4.48 (dd, 1 H, $J_{1,2}$ 3.8 Hz, $J_{2,3}$ 9.85 Hz, H-2), 5.05 (t, 1 H, $J_{3,4}$ and $J_{4,5}$ 9.6 Hz, H-4), 5.35 (t, 1 H, H-3), 5.45 (t, 1 H, $J_{3',4'}$ and $J_{4',5'}$ 7.7 Hz, H-4'), 5.53 (d, 1 H, H-3'), 5.83 (d, 1 H, H-1).

EXAMPLES 5 AND 6

2,3,3',4,4',6'-hexa-O-acetyl-6-O-benzoyl-1'-O-sulfosucrose (5) and 1',2,3,3',4,4'-hexa-O-acetyl-6-O-benzoyl-6'-O-sulfosucrose (6).—6-O-benzoylsucrose (45 mg, 0.1 mmol) was dissolved in anhydrous DMF (1.0 mL) under nitrogen. $Pyr.SO_3$ (16 mg) was added three times at 15-min intervals and the reaction mixture was stirred at room temperature. A 5 μL sample of the reaction mixture was removed, 15 min after the addition of each equivalent of sulfonating agent, quenched with 15 μL water, and analyzed by CE. At the end of the reaction, the reaction mixture was quenched with water and evaporated in vacuo. The residue was acetylated under standard conditions and purified by chromatography on silica gel (9:1 $CHCl_3$—$CH_3OH$) to afford 5 (22%), and 6 (18%). The regioisomeric sulfosucrose 5 and 6 could not be separated. 5 $^1H$ NMR ($CDCl_3$, 500 MHz): δ2.00–2.09 (m, 18 H, 6 C(O)$CH_3$), 4.06 (dd, 1 H, $J_{1a,b}$ 12.1 Hz, H-1'b), 4.16–4.28 (m, 3 H, H-5', H-6'a and H-6'b), 4.24 (d, 1 H, H-1'a), 4.36–4.44 (m, 2 H, H-5 and H-6b), 4.53 (d, 1 H, $J_{6\ a,b}$ 12.1 Hz, H-6a), 4.82 (dd, 1 H, $J_{1,2}$ 3.7 Hz, $J_{2,3}$ 9.7 Hz, H-2), 5.28 (t, 1 H, $J_{3,4}$ and $J_{4,5}$ 9.4 Hz, H-4), 530 (t, 1H, $J_{3',440}$ and $J_{4',5'}$ 7.8 Hz, H-4'), 5.47 (t, 1 H, H-3), 5.61 (d, 1 H, H-3'), 5.73 (d, 1 H, H-1). 6 $^1H$ NMR ($CDCl_3$, 500 MHz): δ2.00–2.09 (m, 18 H, 6 C(O)$CH_3$), 4.23–4.29 (m, 5 H, H-1'a, H-1'b, H-5', H-6'a and H-6'b) 4.36–4.43 (m, 2 H, H-5 and H-6b), 4.66 (d, 1 H, $J_{6a,b}$ 12.2 Hz, H-6a), 4.88 (dd, 1 H, $J_{1,2}$ 3.6 Hz, $J_{2,3}$ 9.7 Hz, H-2), 520 (t, 1 H, $J_{3,4}$ and $J_{4,5}$ 9.3 Hz, H-4), 5.36 (t, 1 H, $J_{3',4'}$ and $J_{4',5'}$ 6.9 Hz H-4') 5.45 (t, 1 H, H-3), 5.61 (d, 1 H, H-3'), 5.65 (d, 1 H, H-1).

EXAMPLE 7

2,3,3',4,4',-penta-O-acetyl-6-O-benzoyl-1',6'-di-O-sulfosucrose (7).—Compound 7 (28%) was isolated from the previous reaction mixture, together with some other minor disulfate regioisomers. $^1H$ NMR ($CDCl_3$, 500 MHz): δ1.99–2.19 (5 s, 15 H, 5 C(O)$CH_3$), 4.02 (dd, 1 H, $J_{1'a,b}$ 11.0 Hz, H-1'b), 4.17 (d, 1 H, H-1'a), 4.22 (m, 1 H, H-6'b), 4.14–4.37 (m, 2 H, H-5' and H-6'a), 4.47–4.50 (m, 2 H, H-5 and H-6b), 4.57 (m, 1 H, $J_{6a,b}$ 12.1 Hz, H-6a), 4.92 (dd, 1 H, $J_{1,2}$ 3.6 Hz, $J_{2,3}$ 10.3 Hz, H-2), 5.21 (t, 1 H, $J_{3,4}$ 10.0 Hz, H-3), 5.34 (t, 1 H, $J_{3',4'}$ and $J_{4',5'}$ 5.6 Hz, H-4'), 5.47 (t, 1 H, $J_{4,5}$ 9.9 Hz, H-4), 5.59 (d, 1 H, H-3') 5.68 (d, 1 H, H-1).

EXAMPLES 8 AND 9

1',2,3',4,4',6'-hexa-O-acetyl-6-O-benzoyl-3-O-sulfosucrose (8) and 1',2,3,3',4',6'-hexa-O-acetyl-6-O-benzoyl-4-O-sulfosucrose (9).—6-O-benzoylsucrose (45 mg, 0.1 mmol) was dissolved in anhydrous DMF (1.0 mL) under nitrogen. $DMF.SO_3$ (15 mg) was added three times at 1.5-h intervals and the reaction mixture was stirred at room temperature. A 5 μL sample of the reaction mixture was removed 15 min, 30 min, 1 h and 1.5 h after addition of each equivalent of sulfonating agents, quenched with 15 μL water, and analyzed by CE. At the end of the reaction, the reaction mixture was quenched with water and evaporated in vacuo. The residue was acetylated under standard conditions and purified by chromatography on silica gel (9:1 $CHCl_3$—$CH_3OH$) to afford 8 (38%), and 9 (32%). The regioisomers 8 and 9 were not separable. 8 $^1H$ NMR ($CDCl_3$, 500 MHz): δ1.99–2.16 (m,18 H 6 C(O)$CH_3$), 4.02 (m, 1 H, H-5'), 4.25 (m, 1 H, H-5), 4.31 (m, 1 H, H-6'b), 4.37 (dd, 1 H, $J_{5,6b}$ 5.5 Hz, $J_{6a,b}$ 12.0 Hz, H-6b), 4.41–4.45 (d, 2 H, H-1'a and H-1'b), 4.55 (m, 1 H, H-6a), 4.59 (m, 1 H, H-6'a), 4.81 (t, 1 H, $J_{2,3}$ and $J_{3,4}$ 9.3 Hz, H-3), 5.15 (d, 1 H, $J_{3',4'}$ 7.6 Hz, H-3'), 5.26 (t, 1 H, $J_{4,5}$ 10.1 Hz, H-4), 5.30 (dd, 1 H, $J_{1,2}$ 3.9 Hz, H-2), 5.76 (t, 1 H, $J_{4',5'}$ 8.0 Hz,H-4'), 6.24 (d, 1 H, H-1). 9 $^1H$ NMR ($CDCl_3$, 500 MHz): δ1.99–2.16 (m, 18 H, 6 $COCH_3$), 4.02 (m, 1 H, H-5') 4.25 (m, 1 H, H-5), 4.31–4.36 (m, 2 H, H-6b and H-6'b), 4.41–4.45 (d, 2 H, H-1'a and H-1'b), 4.54 (m, 1 H, H-6a), 4.55 (t, 1 H, $J_{3,4}$ and $J_{4,5}$ 9.6 Hz, H-4), 4.58–4.61 (m, 1 H, H-6'a), 5.10 (dd, 1 H, $J_{1,2}$ 3.5 Hz, $J_{2,3}$ 10.4 Hz, H-2), 5.18 (d, 1 H, $J^{3',4'}$ 7.8 Hz, H-3'), 5.21 (t, 1 H, $J_{4',5'}$ 9.2 Hz, H-4'), 5.51 (t, 1 H, H-3), 6.30 (d, 1 H, H-1).

EXAMPLE 10

6-O-myristyl-4'-O-sulfosucrose (10).—Sulfonation of 6-O-myristylsucrose (150 mg, 0.27 mmol) with $Pyr.SO_3$ (3×43 mg) afforded 10 in 70% yield; mp=165–170 (decomposition); $[\alpha_D]^{22}$=40.0 (c 0.1, $CH_3OH$); HRFABMS (–ve): Calcd for $C_{26}H_{48}O_{15}S$ [M–H]$^-$ 631.1481; Found 631.1484; $^1H$ NMR (500 MHz, $Me_2SO$-$d_6$): δ0.90 (t, 3 H, $CH_3$), 1.39–1.50 (m, 20 H, 10 $CH_2$), 1.61 (quint., 2 H, C(O)$CH_2CH_2$), 2.35 (t, 2 H, C(O)$CH_2$), 3.02 (t, 1 H, $J_{3,4}$ and $J_{4,5}$ 9.5 Hz, H-4), 3.18 (dd, 1 H, $J_{1,2}$ 3.5 Hz, $J_{2,3}$ 9.6 Hz, H-2), 3.32 (s, 1 H, H-1'b), 3.35 (s, 1 H, H-1'a), 3.48 (t, 1 H, H-3), 3.57 (d, 1 H, $J_{6'a,b}$ 10.7 Hz, H-6'b), 3.69 (d, 1 H, H-6'a), 3.76 (d, 1 H, $J_{3',4'}$ 7.6 Hz, H-3'), 3.87 (t, 1 H, $J_{4',5'}$ 7.5 Hz, H-4'), 3.93–3.99 (m, 2 H, H-5 and H-5'), 4.01 (dd, 1 H, $J_{5,6b}$ 5.4 Hz, $J_{6a,b}$ 10.2 Hz, H-6b), 4.20 (d, 1 H, H-6a), 5.14 (d,1 H, H-1).

EXAMPLE 11

6-O-myristyl-1'-O-sulfosucrose (11).—Sulfonation of 6-O-myristylsucrose (150 mg, 0.27 mmol) with $Pyr.SO_3$ (3×43 mg) afforded 11 in 10% yield; mp=160–165 (decomposition); $[\alpha_D]^{22}$=45.1 (c 0.1 , $CH_3OH$); HRFABMS (–ve): Calcd for $C_{26}H_{48}O_{15}S$ [M–H]$^-$ 631.1481; Found 631.1479; $^1H$ NMR (500 MHz, $Me_2SO$-$d_6$): δ0.96 (t, 3 H, $CH_3$), 1.24–1.36 (m, 20 H, 10 $CH_2$), 1.50 (quint., 2 H, C(O)$CH_2CH_2$), 2.34 (t, 2 H, C(O)$CH_2$), 3.04 (t, 1 H, $J_{3,4}$ and $J_{4,5}$ 9.5 Hz, H-4) 3.17 (dd, 1 H, $J_{1,2}$ 3.5 Hz, $J_{2,3}$ 9.6 Hz, H-2), 3.47 (t, 1 H, H-3), 3.71–3.74 (m, 3 H, H-1'a, H-1'b and H-5'), 3.77 (t, 1 H, $J_{3',4'}$ and $J_{4',5'}$ 7.6 Hz, H-4') 3.84–3.90 (m, 2 H, H-6'a and H-6'b), 3.92 (d, 1 H, H-3'), 3.95–4.00 (m, 1 H, H-5 ), 4.04 (dd, 1 H, $J_{5,6b}$ 6.0 Hz, $J_{6a,b}$ 11.5 Hz, H-6b), 4.17 (d, 1 H, H-6a), 5.12 (d,1 H, H-1).

EXAMPLE 12

6-O-stearyl-4'-O-sulfosucrose (12).—Sulfonation of 6-O-stearylsucrose (150 mg, 0.25 mmol) with $Pyr.SO_3$ (3×39 mg) afforded 12 in 75% yield; mp=183–185 (decomposition); $[\alpha_D]^{22}$=35.0 (c 0.1, $CH_3OH$); HRFABMS (–ve): Calcd for $C_{30}H_{56}O_{15}S$ [M–H]$^-$ 687.2107; Found 687.2105; $^1H$ NMR (500 MHz, $Me_2SO$-$d_6$): δ0.90 (t, 3 H, $CH_3$), 1.39–1.50 (m, 28 H, 14 $CH_2$), 1.60 (quint., 2 H, C(O)$CH_2CH_2$), 2.30 (t, 2 H, C(O)$CH_2$), 3.02 (t, 1 H, $J_{3,4}$ and $J_{4,5}$ 9.6 Hz, H-4) 3.18 (dd, 1 H, $J_{1,2}$ 3.6 Hz, $J_{2,3}$ 9.8 Hz, H-2), 3.34 (s, 1 H, H-1'b), 3.37 (s, 1 H, H-1'a), 3.48 (t, 1 H, H-3), 3.56 (dd, 1 H, H-6'b), 3.69 (d, 1 H, H-6'a), 3.75 (d, 1 H, $J_{3',4}$ 7.6 Hz, H-3'), 3.87 (t, 1 H, $J_{4',5'}$ 7.6 Hz, H-4'), 3.87–3.98 (m, 2 H, H-5 and H-5'), 4.00 (d, 1 H, H-6b), 4.18 (dd, 1 H, $J_{6a,b}$ 11.1 Hz, H-6a), 5.13 (d,1 H, H-1).

EXAMPLE 13

6-O-stearyl-1'-O-sulfosucrose (13).—Sulfonation of 6-O-stearylsucrose (150 mg, 0.25 mmol) with Pyr.SO$_3$ (3×39 mg) afforded 13 in 10% yield; mp=203–206 (decomposition); $[\alpha_D]^{22}$=30.1 (c 0.1, CH$_3$OH); HRFABMS (–ve): Calcd for C$_{30}$H$_{56}$O$_{15}$4S [M–H]$^-$ 687.3262; $^1H$ $NMR$ (500 MHz, D$_2$O): δ0.90 (t, 3 H, CH$_3$), 1.39–1.50 (m, 28 H, 14 CH$_2$), 1.60 (quint., 2 H, C(O)CH$_2$CH$_2$), 2.30 (t, 2 H, C(O)CH$_2$), 3.31 (t, 1 H, $J_{3,4}$ and $J_{4,5}$ 9.7 Hz, H 4), 3.47 (dd, 1 H, $J_{1,2}$ 3.5 Hz, $J_{2,3}$ 9.68 Hz, H-2), 3.69 (t, 1 H, H-3), 3.99–4.02 (m, 3 H, H-1'a, H-1'b and H-5'), 4.06–4.09 (m, 3 H, H-4', H-6'a and H-6'b), 4.14–4.21 (m, 3 H, H-3', H-5 and H-6b), 4.32 (d, 1 H, $J_{6a,b}$ 11.8 Hz, H-6a), 5.32 (d,1 H, H-1).

EXAMPLE 14

1'-O-lauryl-6'-O-sulfosucrose (14).–Sulfonation of 6-O-laurylsucrose (150 mg, 0.29 mmol) with Pyr.SO$_3$ (3×46 mg) afforded 14 in 75% yield; mp=210–215 (decomposition); $[\alpha_D]^{22}$=30.0 (c 0.1, CH$_3$OH); HRFABMS (–ve): Calcd for C$_{24}$H$_{44}$O$_{15}$S [M–H]$^-$ 603.2323; Found 603.2332; $^1$H NMR (500 MHz, Me$_2$SO-d$_6$): δ0.84 (t, 3 H, CH$_3$), 1.23–1.34 (m, 16 H, 8 CH$_2$), 1.51 (quint., 2 H, C(O)CH$_2$CH$_2$), 2.30 (t, 2 H, C(O)CH$_2$), 3.18 (t, 1 H, $J_{3,4}$ and $J_{4,5}$ 9.7 Hz, H-4), 3.27 (dd, 1 H, $J_{1,2}$ 3.4 Hz, $J_{2,3}$ 9.8 Hz, H-2), 3.48 (t, 1 H, H-3), 3.52–3.62 (m, 2 H, H-6a and H-6b), 3.78 (m, 1 H, H-5 ), 3.82–3.98 (m, 3 H, H-3', H-5'and H-6'b), 3.94–3.98 (m, 2 H, H-4', and H-6'a), 4.03 (d, 1 H, $J_{1'a,b}$ 12.1 Hz, H-1'b), 4.10 (d, 1 H, H-1'a), 5.17 (d, 1 H, H-1).

EXAMPLE 15

1'-O-lauryl-6-O-sulfosucrose (15).—Sulfonation of 6-O-laurylsucrose (150 mg, 0.29 mmol) with Pyr.SO$_3$ (3×46 mg) afforded 15 in 10% yield; mp=195–200 (decomposition); $[\alpha_D]^{22}$=35.1 (c 0.1, CH$_3$OH); HRFABMS (–ve): Calcd for C$_{24}$H$_{44}$O$_{15}$S [M–H]$^-$ 603.2323; Found 603.206; $^1$H NMR (500 MHz, Me$_2$SO-d$_6$): δ0.86 (t, 3 H, CH$_3$), 1.23–1.34 (m, 16 H, 8 CH$_2$), 1.51 (quint., 2 H, C(O)CH$_2$CH$_2$) 2.30 (t, 2 H, C(O)CH$_2$), 3.11 (t, 1 H, $J_{3,4}$ $J_{4,5}$ 9.5 Hz, H-4), 3.18 (dd, 1 H, $J_{1,2}$ 3.5 Hz, $J_{2,3}$ 9.5 Hz, H-2), 3.44 (t, 1 H, H-3), 3.58 (m, 1 H, H-5'), 3.74 (m, 1 H, H-5), 3.80–3.85 (m, 5 H, H-3', H-4', H-6'a, H-6b and H-6'b), 3.96 (m, 1 H, H-6a), 4.03 (d, 1 H, $J_{1'a,b}$ 12.0 Hz, H-1'b), 4.12 (d, 1 H, H-1'a), 5.12 (d,1 H, H-1).

EXAMPLE 16

1'-O-myristyl-6'-O-sulfosucrose (16).—Sulfonation of 6-O-myristylsucrose (150 mg, 0.27 mmol) with Pyr.SO$_3$ (3×43 mg) afforded 16 in 70% yield; mp=187–191 (decomposition); $[\alpha_D]^{22}$=45.1 (c 0.1, CH$_3$OH); HRFABMS (–ve): Calcd for C$_{26}$H$_{48}$O$_{15}$S [M–H]$^-$ 631.2636; Found 631.2637; $^1$H NMR (500 MHz Me$_2$SO-d$_6$): δ0.84 (t, 3 H, CH$_3$), 1.23–1.34 (m, 20 H, 10 CH$_2$), 1.51 (quint., 2 H, C(O)CH$_2$CH$_2$), 2.30 (t, 2 H, C(O)CH$_2$), 3.11 (t, 1 h, $J_{3,4}$ and $J_{4,5}$ 9.5 Hz, H-4), 3.17 (dd, 1 H, $J_{1,2}$ 3.4 Hz, $J_{2,3}$ 9.6 Hz, H-2), 3.45 (t, 1 H, H-3), 3.51–3.61 (m, 2 H, H-6a and H-6b), 3.66 (m, 1 H, H-5), 3.73–3.82 (m, 3 H, H-3', H-5'and H-6'b), 3.87–3.93 (m, 3 H, H-1'b, H-4, and H-6'a), 4.11 (d, 1 H, $J_{1'a,b}$ 12.0 Hz, H-1'a), 5.12 (d, 1 H, H-1).

EXAMPLE 17

1'-O-myristyl-6-O-sulfosucrose (17).- Sulfonation of 6-O-myristylsucrose (150 mg, 0.27 mmol) with Pyr.SO$_3$ (3×43 mg) afforded 17 in 10% yield; mp=195–200 (decomposition); $[\alpha_D]^{22}$=40.0 (c 0.1, CH$_3$OH); HRFABMS (–ve): Calcd for C$_{26}$H$_{48}$O$_{15}$S [M–H]$^-$ 631.1481; Found 631.1485; $^1$H NMR (500 MHz, Me$_2$SO-d$_6$): δ0.86 (t, 3 H, CH$_3$), 1.28–1.40 (m, 20 H, 10 CH$_2$), 1.50 (quint., 2 H, C(O)CH$_2$CH$_2$), 2.30 (t, 2 H, C(O)CH$_2$), 3.11 (t, 1 H, $J_{3,4}$ and $J_{4,5}$ 9.5 Hz, H-4), 3.18 (dd, 1 H, $J_{1,2}$ 3.4 Hz, $J_{2,3}$ 9.5 Hz, H-2), 3.44 (t, 1 H, H-3), 3.58 (m, 1 H, H-5'), 3.74 (m, 1 H, H-5), 3.80–3.85 (m, 2 H, H-6'a and H-6'b), 3.91–4.03 (m, 5 H, H-1'b, H-3', H-4', H-6a, H-6b), 4.09 (d, 1 H, $J_{1'a,b}$ 12.0 Hz, H-1'a), 5.13 (d, 1 H, H-1).

EXAMPLE 18

1'-O-stearyl-6'-O-sulfosucrose (18).—Sulfonation of 6-O-stearylsucrose (150 mg, 0.25 mmol) with Pyr.SO$_3$ (3×39 mg) afforded 18 in 67% yield; mp=175–180 (decomposition); $[\alpha_D]^{22}$=35.1 (c 0.1, CH$_3$OH); HRFABMS (–ve): Calcd for C$_{30}$H$_{56}$O$_{18}$S [M–H]$^-$ 687.2107; Found 687.2094; $^1$H NMR (500 MHz, Me$_2$SO-d$_6$): δ0.92 (t, 3 H, CH$_3$), 1.22–1.36 (m, 28 H, 14 CH$_2$), 1.60 (quint., 2 H, C(O)CH$_2$CH$_2$), 2.36 (t, 2 H, C(O)CH$_2$), 3.17 (t, 1 H, $J_{3,4}$ and $J_{4,5}$ 9.5 Hz, H-4), 3.23 (dd, 1 H, $J_{1,2}$ 3.4 Hz, $J_{2,3}$ 9.6 Hz, H-2), 3.51 (t, 1 H, H-3), 3.53–3.61 (m, 2 H, H-6a and H-6b), 3.68 (m, 1 H, H-5), 3.76 (m, 1 H, H-5'), 3.82–3.88 (m, 2 H, H-3' and H-6'b), 3.92–3.97 (m, 2 H, H-4', and H-6'a), 4.03 (dd, 1 H, $J_{1'a,b}$ 12.0 Hz H-1'b), 4.17 (dd, 1 H, H-1'a), 5.19 (d, 1 H, H-1).

EXAMPLE 19

1'-O-stearyl-6-O-sulfosucrose (19).—Sulfonation of 6-O-stearylsucrose (150 mg, 0.25 mmol) with Pyr.SO$_3$ (3×39 mg) afforded 19 in 10% yield; mp=170–175 (decomposition); $[\alpha_D]^{22}$=40.0 (c 0.1, CH$_3$OH); HRFABMS (–ve): Calcd for C$_{30}$H$_{56}$O$_{18}$ S [M–H]$^-$ 687.2107; Found 687.2102; $^1$H NMR (500 MHz, Me$_2$SO-d$_6$): δ0.92 (t, 3 H, CH$_3$), 1.22–1.36 (m, 28 H, 14 CH$_2$), 1.60 (quint., 2 H, C(O)CH$_2$CH$_2$), 2.36 (t, 2 H, C(O)CH$_2$), 2.30 (t, 2 H, C(O)CH$_2$), 3.17 (t, 1 H, $J_{3,4}$ and $J_{4,5}$ 9.6 Hz, H-4), 3.19 (dd, 1 H, $J_{1,2}$ 3.3 Hz, $J_{2,3}$ 9.6 Hz, H-2), 3.46 (t, 1 H, H-3), 3.57 (m, 1 H, H-5'), 3.74 (m, 1 H, H-5), 3.79–3.88 (m, 5 H, H-3', H-4', H-6b, H-6'a and H-6'b), 3.97 (m, 1 H, H-6a), 4.03 (dd, 1 H, $J_{1'a,b}$ 12.1 Hz, H-1'b) 4.11 (d, 1 H, H-1'a), 5.13 (d,1 H, H-1).

EXAMPLES 20 AND 21

Preparation of 1'2:4,6-di-O-isopropylidenesucrose (20) and 4,6-mono-O-isopropylidenesucrose (21) [53].—To a solution of sucrose (1.0 g, 2.9 mmol) in anhydrous DMF (10 mL) under argon were added 2,2'-dimethoxypropane (4.3 mL, 35.1 mmol) and a catalytic amount of p-toluenesulfonic acid. After 2 h at room temperature, the reaction mixture was neutralized by addition of NEt$_3$ and the mixture concentrated in vacuo. Purification by chromatography on silica gel (9:1 CHCl$_3$—CH$_3$OH) afforded 20 (566 mg, 46%) and 21 (504 mg, 45%) as white amorphous solids. Compound 21 was used without further characterization.

EXAMPLE 22

Preparation of 1',2,3,3',4',6'-hexa-O-acetylsucrose (22) [54].—To a solution of 21 (595 mg, 1.56 mmol) in anhydrous Pyr (5 mL) acetic anhydride (1.4 mL, 14.0 mmol) was added under nitrogen. After 12 h at room temperature, the reaction mixture was quenched with CH$_3$OH and concentrated in vacuo. The resulting residue was dissolved in 60% acetic acid and heated at 80° C. for 15 min. After concentration in vacuo and purification by chromatography on silica gel 1:2 hexane-ethyl acetate) 22 was obtained in 91% yield (848 mg). $^1$H NMR (500 MHz, CDCl$_3$): δ2.10–2.19 (m, 18 H, 6 OAc), 3.65 (t, 1 H, J$_{3,4}$ and J$_{4,5}$ 9.5 Hz, H-4), 3.81 (dd, 1 H, J$_{5,6b}$ 5.0 Hz, J$_{6a,b}$ 12 Hz, H-6b), 3.92 (d, 1 H, H-6a), 4.01 (m, 1 H, H-5), 4.16–4.18 (dd, 2 H, H-1'a and H-1'b), 4.22 (m, 1 H, H-6'b), 4.23 (m, 1 H, H-5'), 4.88 (m, 1 H, H-6'a), 4.77 (dd, 1 H, J$_{1,2}$ 3.5 Hz, J$_{2,3}$ 9.8 Hz, H-2), 5.33 (t, 1 H, H-3), 5.39 (t, 1 H, J$_{3',4'}$ and J$_{4',5'}$ 6.0 Hz, H-4'), 5.45 (d, 1 H, H-3'), 5.64 (d, 1 H, H-1). The intermediate hexaacetylsucrose was used without further purification.

EXAMPLES 23 AND 24

1',2,3,3',4',6'-hexa-O-acetylsucrose 4,6-cyclic sulfite (23) and (24).—To a solution of 22 (141 mg, 0.24 mmol) in anhydrous EtOAc (2 mL) and under nitrogen were added SOCl$_2$ (19 μL, 0.25 mmol) and anhydrous Pyr (20 μL, 0.50 mmol). After 1 h at room temperature, SOCl$_2$ (10 μL, 0.13 mmol) and anhydrous Pyr (10 μL, 0.25 mmol) were added. After 30 more minutes, the reaction mixture was quenched by addition of water and extracted with EtOAc. The organic extract was washed with water, dried over Na$_2$SO$_4$, filtered and concentrated in vacuo. Purification by chromatography on silica gel (1:2 hexane-EtOAc) afforded 23 (28 mg, 18%) and 24 (64 mg, 42%) as white amorphous solids. 23 [α$_D$]$^{22}$=69.1 (c 0.1, CHCl$_3$); FABMS (+ve) m/z 641, 663 [M+H$^+$]$^+$; [M+Na$^+$]$^+$; $^1$H NMR (500 MHz, CDCl$_3$): δ2.07–2.20 (6s, 18 H, 6 OAc), 4.13 (overlapped dd, 1 H, H-6b), 4.13–4.20 (dd, 2 H, H-1'a and H-1'b), 4.21 (m, 1 H, H-5'), 4.24 (dd, overlapped with H-5, 1 H, H-6'b), 4.32 (dd, 1 H, J$_{5',6'a}$ 3.8 Hz, J$_{6',a,b}$ 12 Hz, H-6'a), 4.20 (m, 1 H, H-5), 4.68 (t, 1 H, J$_{6a,b}$ 10.7 Hz, H-6a), 4.77 (t, 1 H, J$_{3,4}$ and J$_{4,5}$ 10.0 Hz, H-4), 4.85 (dd, 1 H, J$_{1,2}$ 3.8 Hz, J$_{2,3}$ 10.0 Hz, H-2), 5.38 (t, 1 H, J$_{3',4'}$ and J$_{4',5'}$ 6.0 Hz, H-4'), 5.45 (d, 1 H, H-3'), 5.50 (t, 1 H, H-3), 5.75 (d, 1 H, H-1) Anal. Calcd for C$_{24}$H$_{32}$O$_{18}$S (640.6) C, 45.00; H, 5.04; Found C, 45.12; H, 5.08; 24 [α$_D$]$^{22}$=47.0 (c 0.1, CHCl$_3$); FABMS (+ve) m/z 641, 663 [M+H$^+$]$^+$ [M+Na$^+$]$^+$; $^1$H NMR (500 MHz, CDCl$_3$): δ2.08–2.22 (6 s, 18 H, 6 OAc), 4.10 (t, 1 H, J$_{3,4}$ and J$_{4,5}$ 9.9 Hz, H-4), 4.12 (m, 1 H, H-6b), 4.13–4.19 (dd, 2 H, H-1'a and H-1'b), 4.19 (m, 1 H, H-5'), 4.24 (m, 1 H, H-6'b), 4.29 (dd, 1 H, J$_{5',6'a}$ 4.5 Hz, J$_{6'a,b}$ 12 Hz, H-6'a), 4.66 (dd, 1 H, J$_{5,6a}$ 6.2 Hz, J$_{6a,b}$ 11.1 Hz, H-6a), 4.75 (m, 1 H, H-5), 4.82 (dd, 1 H, J$_{1,2}$ 3.8 Hz, J$_{2,3}$ 10.1 Hz, H-2), 5.36 (t, 1 H, J$_{3',4'}$ and J$_{4',5'}$ 5.9 Hz, H-4'), 5.45 (d, 1 H, H-3'), 5.54 (t, 1 H, H-3), 5.71 (d, 1 H, H-1). Anal. Calcd for C$_{24}$H$_{32}$O$_{18}$S (640.6) C, 45.00; H, 5.04; Found C, 45.03; H, 5.18.

EXAMPLE 25

1',2,3,3',4',6'-hexa-O-acetylsucrose 4,6-cyclic sulfate (25).—To a solution of 23 or 24 (307 mg, 0.48 mmol) in a mixture of H$_2$O—CH$_3$CN (3 mL–2 mL) was added RuCl$_3$ (catalytic amount) and NaIO$_4$ (205 mg, 0.96 mmol). After 1 h at room temperature, the reaction mixture was extracted with CHCl$_3$. The organic extract was washed with water, dried over Na$_2$SO$_4$, filtered and concentrated in vacuo. Purification by chromatography on silica gel (1:2 hexane-EtOAc) afforded 25 (299 mg, 95%). [α$_D$]$^{22}$=56.0 (c 0.1, CHCl$_3$); FABMS (+ve) m/z 679 [M+Na$^+$]$^+$; HRFABMS (+ve): Calcd for C$_{24}$H$_{32}$O$_{19}$S [M+Li]$^+$ 663.1419; Found 663.1426. $^1$H NMR (500 MHz, CDCl$_3$): δ2.04–2.19 (6 s, 18 H, 6 OAc), 4.12 (dd, 1 H, J$_{6'a,b}$ 11.7 Hz, H-6'b), 4.19–4.24 (m, 3 H, H-1'a, H-1'b and H-5'), 4.33 (dd, 1 H, J$_{5',6'a}$ 3.2 Hz, H-6'a), 4.58–4.69 (m, 4 H, H-4, H-5, H-6a and H-6b), 4.80 (dd, 1 H, J$_{1,2}$ 3.75 Hz, J$_{2,3}$ 10.0 Hz, H-2), 5.35 (t, 1 H, J$_{3',4'}$ and J$_{4',5'}$ 5.8 Hz, H-4'), 5.44 (d, 1 H, H-3'), 5.58 (t, 1 H, J$_{3,4}$ 9.7 Hz, H-3), 5.47 (d, 1 H, H-1).

EXAMPLE 26

Sucrose 4,6-cyclic sulfate (26).—To a solution of 25 (286 mg, 0.44 mmol) in anhydrous methanol (5 mL) and under argon was added NEt$_3$ (0.73 mL, 5.23 mmol). After 15 h at room temperature, the reaction mixture was neutralized with resin IR 120 (H$^+$), filtered and concentrated in vacuo. Purification by chromatography on silica gel (4:1 CHCl$_3$—CH$_3$OH) afforded 26 (155 mg, 88%). [α$_D$]$^{22}$=26.0 (c 0.1, CH$_3$OH); FABMS (+ve) m/z 411 [M+Li$^+$]$^+$; HRFABMS (+ve): Calcd for C$_{12}$H$_{20}$O$_{13}$S [M+Li]$^+$ 411.0785; Found 411.0792. $^1$H NMR (500 MHz, CD$_3$OD): δ3.55 (dd, 1 H, J$_{1,2}$ 3.8 Hz, J$_{2,3}$ 10.1 Hz, H-2), 3.60 (s, 1 H, H-1'b), 3.63 (s, 1 H, H-1'a), 3.66 (dd, 1 H, J$_{5',6'a}$ 4.5 Hz, J$_{6'a,b}$ 12.0 Hz, H-6'b), 3.74–3.79 (m, 2 H, H-6'a and H-5'), 4.00 (t, 1 H, J$_{3,4}$ 9.3 Hz, H-3), 4.02 (t, 1 H, J$_{3',4'}$ and J$_{4',5'}$ 8.4 Hz, H-4'), 5.47 (d, 1 H, H-3'), 4.41 (t, 1 H, J$_{4,5}$ 9.3 Hz, H-4), 4.54–4.60 (m, 3 H, H-5, H-6a and H-6b), 5.47 (d, 1 H, H-1).

EXAMPLE 27

Sucrose 4,6-cyclic sulfite (27).—Sucrose (100 mg, 0.29 mmol) was dissolved, at 80° C., in anhydrous DMF (1 mL). The solution was cooled at room temperature, and EtOAc (1 mL) was added under argon. To the resulting suspension was added SOCl$_2$ (22 μL, 0.31 mmol) and anhydrous Pyr (50 μL, 0.61 mmol). After 1 h, SOCl$_2$ (22 μL, 0.31 mmol) was added. After 1 additional h, the reaction mixture was neutralized by addition of NEt$_3$, and concentrated in vacuo. Purification by chromatography on silica gel (4:1 CHCl$_3$—CH$_3$OH) afforded 27 (23 mg, 20%). [α$_D$]$^{22}$=20.0 (c 0.1, CH$_3$OH); Calcd for C$_{12}$H$_{20}$O$_{12}$S [M+Li]$^+$ 395.0791; Found 395.0796. $^1$H NMR (500 MHz, CD$_3$OD): δ3.56 (dd, 1 H, J$_{1,2}$=4.0 Hz, J$_{2,3}$ 9.5 Hz, H-2), 3.63–3.68 (m, 3 H, H-1'a, H-1'b and H-6'b), 3.74–3.80 (m, 2 H, H-5' and H-6'a), 3.92 (t, 1 H, J$_{3,4}$ 9.5 Hz, H-3), 4.03 (t, 1 H, J$_{3',4'}$ and J$_{4',5'}$ 8.5 Hz, H-4'), 4.04 (m, 1 H, H-6'b), 4.12 (d, 1 H, H-3'), 4.33 (m, 1 H, H-5), 4.48 (t, 1 H, J$_{4,5}$ 9.9 Hz, H-4), 4.55 (t, 1 H, J$_{6a,b}$ 11.1 Hz, H-6a), 5.43 (d, 1 H, H-1).

EXAMPLE 28

6-O-palmityl-4-O-sulfosucrose (28).—Reaction of sucrose cyclic sulfate 26 (33 mg, 0.08 mmol) with palmitic acid (23 mg, 0.09 mmol) led to 28 as an amorphous white solid in 75% yield. [α$_D$]$^{22}$=40.1 (c 0.1, CH$_3$OH); HRFABMS (−ve): Calcd for C$_{28}$H$_{52}$O$_{15}$S [M−H]$^-$ 659.2949; Found 659.2946; $^1$H NMR (500 MHz, Me$_2$SO-d$_6$): δ0.86 (t, 3 H, CH$_3$), 1.25–1.30 (m, 22 H, 11 CH$_2$), 1.51–1.53 (quint., 2 H, C(O)CH$_2$CH$_2$), 2.30 (t, 2 H, C(O)CH$_2$), 3.32 (dd, 1 H, J$_{1,2}$ 3.75 Hz, J$_{2,3}$ 9.4 Hz, H-2), 3.40 (s, 2 H, H-1'a,b), 3.53 (m, 1 H, H-6'b), 3.61 (m, 2 H, H-5' and H-6'a), 3.56 (t, 1 H, J$_{3',4'}$ and J$_{4',5'}$ 7.8 Hz, H-4'), 3.77 (t, 1 H, J$_{3,4}$ 9.2 Hz, H-3), 3.84 (t, 1 H, J$_{4,5}$ 9.9 Hz, H-4), 3.87 (d, 1 H, H-3'), 3.98 (dd, 1 H, J$_{5,6b}$ 6.8 Hz, J$_{6a,b}$ 11.9 Hz, H-6b), 4.07 (m, 1 H, H-5), 4.24 (d, 1 H, H-6a), 5.19 (d, 1 H, H-1).

EXAMPLE 29

6-O-stearyl-4-O-sulfosucrose (29).—Reaction of sucrose cyclic sulfate 26 (109 mg, 0.27 mmol) with stearic acid (53 mg, 0.32 mmol) led to 29 as an amorphous white solid in 72% yield. [α$_D$]$^{22}$=35.0 (c 0.1, CH$_3$OH); HRFABMS (−ve): Calcd for C$_{30}$H$_{56}$O$_{15}$S [M−H]$^-$ 687.3262; Found 687.3276; $^1$H NMR (500 MHz, CD$_3$OD): δ0.95 (t, 3 H, CH$_3$), 1.22–1.38 (m, 28 H, 14 CH$_2$), 1.63 (m, 2 H, C(O)CH$_2$CH$_2$), 2.38 (t, 2 H, C(O)CH$_2$), 3.59 (dd, 1 H, J$_{1,2}$ 3.82 Hz, J$_{2,3}$ 9.8 Hz, H-2), 3.62 (d, 1 H, J$_{1'a,b}$ 12.2 Hz, H-1'b), 3.68 (d, 1 H, H-1'a), 3.76–3.82 (m, 3 H, H-5', H-6'a and H-6'b), 4.02 (t, 1

H, $J_{3',4'}$ and $J_{4',5'}$ 7.6 Hz, H-4'), 4.04 (t, 1 H, $J_{3,4}$ 8.2 Hz, H-3), 4.07 (d, 1 H, H-3'), 4.19–4.21 (m, 1 H, H-5), 4.22 (t, 1 H, $J_{4,5}$ 8.2 Hz, H-4), 4.27 (dd, 1 H, $J_{5,6b}$ 4.7 Hz, $J_{6a,b}$ 12.1 Hz, H-6b), 4.41 (d, 1 H, H-6a), 5.42 (d,1 H, H-1).

EXAMPLE 30

6-O-eicosanoyl-4-O-sulfosucrose (30).—Reaction of sucrose cyclic sulfate 26 (27 mg, 0.07 mmol) with eicosanoic acid (25 mg, 0.08 mmol) led to 31 as an amorphous white solid in 60% yield. $[\alpha_D]^{22}$=28 (c 0.1, $CH_3OH$); HRFABMS (–ve): Calcd for $C_{32}H_{60}O_{15}S$ [M–H]$^-$ 715.3575; Found 715.3562; $^1H$ NMR (500 MHz, $CD_3OD$): δ0.90 (t, 3 H, $CH_3$), 1.25–1.35 (m, 32 H, 16 $CH_2$), 1.61 (quint., 2 H, $C(O)CH_2CH_2$), 2.37 (t, 2 H, $C(O)CH_2$), 3.54 (dd, 1 H, $J_{1,2}$ 3.7 Hz, $J_{2,3}$ 9.7 Hz, H-2), 3.59 (d, 1 H, $J_{1'a,b}$ 12.3 Hz, H-1'b), 3.64 (d, 1 H, H-1'a), 3.72–3.79 (m, 3 H, H-5', H-6'a and H-6'b), 3.98 (t, 1 H, $J_{3',4'}$ and $J_{4',5'}$ 8.1 Hz, H-4'), 4.01 (t, 1 H, $J_{3,4}$ 9.7 Hz, H-3), 4.07 (d, 1 H, H-3'), 4.19–4.24 (m, 3 H, H-4, H-5 and H-6b), 4.40 (d, 1 H, $J_{6a,b}$ 11.4 Hz, H-6a), 5.39 (d,1 H, H-1).

EXAMPLE 31

6-O-deoxy-6-O-hexadecylamine-4-O-sulfosucrose (31).—Reaction of sucrose cyclic sulfate 26 (39 mg, 0.10 mmol) with hexadecylamine (28 mg, 0.11 mmol) led to 31 as an amorphous white solid in 76% yield. $[\alpha_D]^{22}$=–18.0 (c 0.1, $CH_3OH$); HRFABMS (–ve): Calcd for $C_{28}H_{55}NO_{13}S$ [M–H]$^-$ 644.3316; Found 644.3323; $^1H$ NMR (500 MHz, $CD_3OD$): δ0.91 (t, 3 H, $CH_3$), 1.25–1.43 (m, 26 H, 13 $CH_2$), 1.68 (quint., 2 H, $NCH_2CH_2$), 2.98 (t, 2 H, $NCH_2$), 3.17(dd, 1 H, $J_{5,6b}$ 8.1 Hz, $J_{6a,b}$ 13.1 Hz, H-6b), 3.44 (dd, 1 H, $J_{5,6a}$ 2.75 Hz, H-6a), 3.58 (dd, 1 H, $J_{1,2}$ 4.0 Hz, $J_{2,3}$ 9.7 Hz, H-2), 3.68 (dd, 1 H, $J_{5',6'b}$ 6.87 Hz, $J_{6'a,b}$ 11.8 Hz, H-6'b), 3.74–3.80 (m, 3 H, H-1'a, H-1'b and H-5'), 3.83 (dd, 1 H, $J_{5,6'a}$ 2.6 Hz, H-6'a), 3.91 (t, 1 H, $J_{3,4}$ 9.3 Hz, H-3), 3.98 (t, 1 H, $J_{3',4'}$ and $J_{4',5'}$ 7.3 Hz, H-4'), 4.07 (t, 1 H, $J_{4,5}$ 8.8 Hz, H-4), 4.14 (d, 1 H, H-3'), 4.32 (m, 1 H, H-5), 5.46 (d,1 H, H-1).

EXAMPLE 32

6-O-deoxy-6-O-octadecylamine-4-O-sulfosucrose (32).—Reaction of sucrose cyclic sulfate 26 (58 mg, 0.14 mmol) with octadecylamine (47 mg, 0.17 mmol) led to 32 as an amorphous white solid in 60% yield. $[\alpha_D]^{22}$=48.0 (c 0.1, $CH_3OH:CHCl_3$ 1:1); HRFABMS (–ve): Calcd for $C_{30}H_{59}NO_{13}S$ [M–H]$^-$ 672.3629; Found 672.3619; $^1H$ NMR (500 MHz, $CD_3OD$): δ0.90 (t, 3 H, $CH_3$), 1.26–1.42 (m, 30 H, 15 $CH_2$), 1.68 (quint., 2 H, $NCH_2CH_2$), 3.00 (t, 2 H, $NCH_2$), 3.18 (dd, 1 H, $J_{5,6b}$ 8.3 Hz, $J_{6a,b}$ 13.3 Hz, H-6b), 3.45 (dd, 1H, $J_{5,6a}$ 2.6 Hz, H-6a), 3.56 (dd, 1 H, $J_{1,2}$ 3.8 Hz, $J_{2,3}$ 9.70 Hz, H-2), 3.68 (dd, 1 H, $J_{5',6'b}$ 7.2 Hz, $J_{6'a,b}$ 11.5 Hz, H-6'b), 3.74–3.79 (m, 3 H, H-1'a, H-1'b and H-5'), 3.83 (dd, 1 H, $J_{5,6'a}$ 2.7 Hz, H-6'a), 3.89 (t, 1 H, $J_{3,4}$ 9.3 Hz, H-3), 3.97 (t, 1 H, $J_{3',4'}$ and $J_{4',5'}$ 7.5 Hz, H-4'), 4.06 (t, 1 H, $J_{4,5}$ 8.9 Hz, H-4), 4.14 (d, 1 H, H-3'), 4.32 (m, 1 H, H-5), 5.46 (d,1 H, H-1).

What is claimed is:

1. A sulfonated sucrose having the structure:

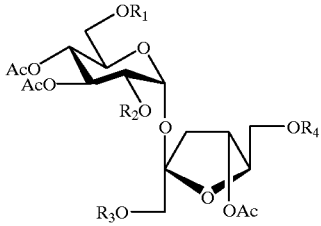

wherein $R_1$–$R_4$ may be the same or different and are selected from the group consisting of —$SO_3H$, —OAc, an ether having one to ten carbon atoms, silyl, and an ester having one to ten carbon atoms, with the proviso that one and only one of $R_1$–$R_4$ consists of —$SO_3H$.

2. A sulfonated sucrose as claimed in claim 1, which is 1',2,3,3',4,4',6'-hepta-O-acetyl-6-O-sulfosucrose.

3. A sulfonated sucrose as claimed in claim 1, which is 2,3,3',4,4',6,6'-hepta-O-acetyl-1'-O-sulfosucrose.

4. A sulfonated sucrose as claimed in claim 1, which is 1',2,3,3',4,4',6-hepta-O-acetyl-6'-O-sulfosucrose.

5. A sulfonated sucrose as claimed in claim 1, which is 1',3,3',4,4',6,6'-hepta-O-acetyl-2-O-sulfosucrose.

6. A sulfonated sucrose having the structure:

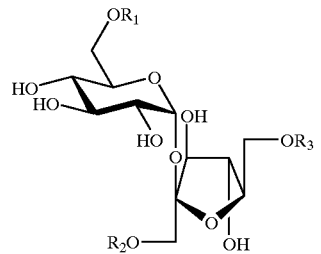

wherein $R_1$ is benzoyl or substituted benzoyl and one of $R_2$ and $R_3$ is —$SO_3H$ and the other is selected from the group consisting of hydrogen and —$SO_3H$.

7. A sulfonated sucrose as claimed in claim 6, which is 2,3,3',4,4',6'-hexa-O-acetyl-6-O-benzoyl-1'-O-sulfosucrose.

8. A sulfonated sucrose as claimed in claim 6, which is 1',2,3,3',4,4'-hexa-O-acetyl-6-O-benzoyl-6'-O-sulfosucrose.

9. A sulfonated sucrose as claimed in claim 6, which is 2,3,3',4,4,'-penta-O-acetyl-6-O-benzoyl-1',6'-di-O-sulfosucrose.

10. A sulfonated sucrose as claimed in claim 6, which is 1',2,3',4,4',6-hexa-O-acetyl-6-O-benzoyl-3-O-sulfosucrose.

11. A sulfonated sucrose as claimed in claim 6, which is 1',2,3,3',4',6'-hexa-O-acetyl-6-O-benzoyl-4-O-sulfosucrose.

12. A sulfonated sucrose having the structure:

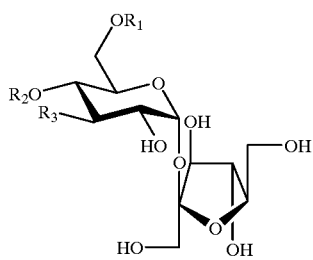

wherein $R_1$ is a benzoyl or substituted benzoyl and $R_2$ are $R_3$ are different and are selected from the group consisting of hydrogen and —$SO_3H$.

13. A sulfonated sucrose as claimed in claim 12, which is 1',2,3',4,4',6'-hexa-O-acetyl-6-O-benzoyl-3-O-sulfosucrose.

14. A sulfonated sucrose as claimed in claim 12, which is 1',2,3,3',4',6'-hexa-O-acetyl-6-O-benzoyl-4-O-sulfosucrose.

15. A surfactant having the structure:

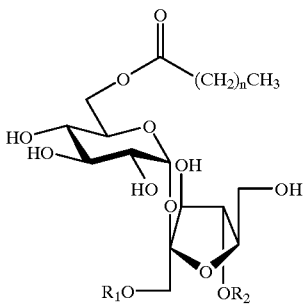

wherein $R_1$ and $R_2$ are different and are selected from the group consisting of hydrogen and —$SO_3H$, and wherein n is 5 to 25.

16. A surfactant as claimed in claim 15, which is 6-O-myristyl-4'-O-sulfosucrose.

17. A surfactant as claimed in claim 15, which is 6-O-myristyl-1'-O-sulfosucrose.

18. A surfactant as claimed in claim 15, which is 6-O-stearyl-4'-O-sulfosucrose.

19. A surfactant as claimed in claim 15, which is 6-O-stearyl-1'-O-sulfosucrose.

20. A surfactant having the structure:

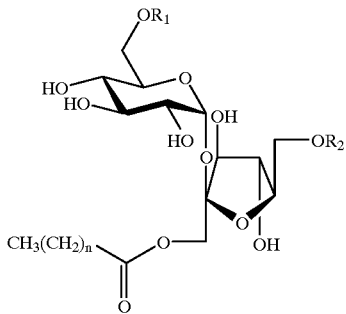

wherein $R_1$ and $R_2$ are different and are selected from the group consisting of hydrogen and —$SO_3H$, and wherein n is 5 to 25 carbon atoms.

21. A surfactant as claimed in claim 20, which is 1'-O-lauryl-6'-O-sulfosucrose.

22. A surfactant sucrose as claimed in claim 20, which is 1'-O-lauryl-6-O-sulfosucrose.

23. A surfactant sucrose as claimed in claim 20, which is 1'-O-myristyl-6'-O-sulfosucrose.

24. A surfactant sucrose as claimed in claim 20, which is 1'-O-myristyl-6-O-sulfosucrose.

25. A surfactant sucrose as claimed in claim 20, which is 1'-O-stearyl-6'-O-sulfosucrose.

26. A surfactant sucrose as claimed in claim 20, which is 1'-O-stearyl-6-O-sulfosucrose.

27. A surfactant having the structure:

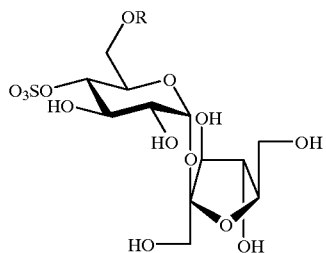

wherein R is selected from the group consisting of —OC(O)—($CH_2$)$nCH_3$ and —$NH^+_2$—$(CH_2)_nCH_3$ and n is an integer from 5 to 25.

28. A surfactant as claimed in claim 27, which is 6-O-palmityl-4-O-sulfosucrose.

29. A surfactant as claimed in claim 27, which is 6-O-stearyl-4-O-sulfosucrose.

30. A surfactant as claimed in claim 27, which is 6-O-eicosanoyl-4-O-sulfosucrose.

31. A surfactant as claimed in claim 27, which is 6-O-deoxy-6-O-hexadecylamine-4-O-sulfosucrose.

32. A surfactant as claimed in claim 27, which is 6-O-deoxy-6-O-octadecylamine-4-O-sulfosucrose.

33. A detergent comprising a surfactant as claimed in claim 15.

34. A detergent comprising a surfactant as claimed in claim 19.

35. A detergent comprising a surfactant as claimed in claim 27.

36. An intermediate cyclic sulfate having the structure:

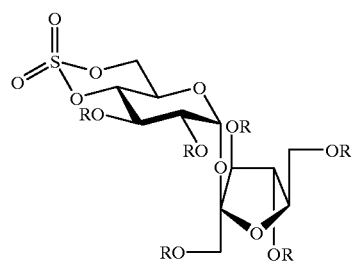

wherein R is hydrogen or a hydroxyl protecting group selected from the group consisting of -Ac, -Bz, Bn, silyl.

37. An intermediate cyclic sulfite having the structure:

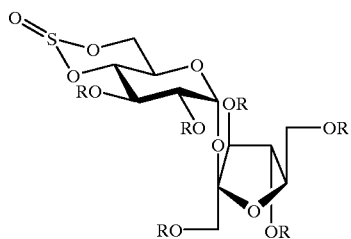

wherein R is be hydrogen or a hydroxyl protecting group selected from the group consisting of -Ac, -Bz, Bn, silyl.

38. A process for synthesizing a 4,6-cyclic sulfite derivative of sucrose by reacting sucrose or 2,3,1',3',4',6'-hexa-O-acetylsucrose with thionyl chloride in the presence of base.

39. A process for synthesizing a 4,6-cyclic sulfate derivative of sucrose by oxidizing a 4,6-cyclic sulfite derivative of sucrose with $RuCl_3$(catalytic)/$NaIO_4$.

40. A process for synthesizing a sucrose derivative that is 6-O-substituted with a nucleophilic reagent and is 4-O-sulfonated comprising opening a 4,6-cyclic sulfate sucrose or a derivative thereof with a nucleophile, wherein the nucleophile is selected from the group consisting of fatty acyl and aminoalkyl compounds containing from 4 to 30 carbons.

41. A process as claimed in claim 40, wherein the fatty acyl or aminoalkyl compound has from 14–20 carbons and an amine or carboxylate group as a nucleophilic moiety.

* * * * *